US012745790B2

(12) United States Patent
Cabezas-Cruz et al.

(10) Patent No.: US 12,745,790 B2
(45) Date of Patent: Sep. 29, 2026

(54) **USE OF *E. COLI* STRAINS EXPRESSING HIGH LEVEL OF α-GAL TO MODULATE IMMUNITY AND PROVIDE PROTECTION AGAINST INFECTIOUS DISEASES IN ANIMALS**

(71) Applicants: Institut national de recherche pour l'agriculture, l'alimentation et l'environnement, Paris (FR); ECOLE NATIONALE VETERINAIRE D'ALFORT, Maison Alfort (FR); UNIVERSITE PARIS EST CRETEIL VAL DE MARNE, Creteil (FR); CONSEJO SUPERIOR DE INVESTIGACIONES CIENTIFICAS, Madrid (ES); Biologicke Centrum AV CR v. v. i., Ceske Budejovice (CZ)

(72) Inventors: Alejandro Cabezas-Cruz, Alfortville (FR); Lourdes Mateos-Hernandez, Alfortville (FR); Astrid Sibylle Holzer, Ceske Budejovice (CZ); Luis Bermudez-Humaran, Bievres (FR); Veronica Risco-Castillo, Alfortville (FR); Jose de Jesus De La Fuente-Garcia, Cuidad Real (ES); Edgar Torres-Maravilla, Paris (FR); Jacques Guillot, Le Chatelet en Brie (FR)

(73) Assignees: Institut national de recherche pour l'agriculture, l'alimentation et l'environnement, Paris (FR); ECOLE NATIONALE VETERINAIRE D'ALFORT, Maison Alfort (FR); UNIVERSITE PARIS EST CRETEIL VAL DE MARNE, Creteil (FR); CONSEJO SUPERIOR DE INVESTIGACIONES CIENTIFICAS, Madrid (ES); Biologicke Centrum AV CR v. v. i., Geske Budejovice (CZ)

( * ) Notice: Subject to any disclaimer, the term of this patent is extended or adjusted under 35 U.S.C. 154(b) by 594 days.

(21) Appl. No.: 17/999,668

(22) PCT Filed: Jun. 3, 2021

(86) PCT No.: PCT/EP2021/064947

§ 371 (c)(1),
(2) Date: Nov. 22, 2022

(87) PCT Pub. No.: WO2021/245207

PCT Pub. Date: Dec. 9, 2021

(65) Prior Publication Data

US 2023/0232882 A1 Jul. 27, 2023

(30) Foreign Application Priority Data

Jun. 5, 2020 (EP) .................................... 20305597

(51) Int. Cl.

*A61K 39/02* (2006.01)
*A23K 50/75* (2016.01)
*A23K 50/80* (2016.01)
*A23L 33/135* (2016.01)
*A61K 9/00* (2006.01)
*A61K 39/108* (2006.01)
*A61K 39/00* (2006.01)

(52) U.S. Cl.

CPC ............ *A23L 33/135* (2016.08); *A23K 50/75* (2016.05); *A23K 50/80* (2016.05); *A61K 9/0053* (2013.01); *A61K 39/0258* (2013.01); *A61K 2039/522* (2013.01)

(58) Field of Classification Search

None
See application file for complete search history.

(56) References Cited

PUBLICATIONS

Cabezas-Cruz, et al. Tick galactosyltransferases are involved in α-Gal synthesis and play a role during Anaplasma phagocytophilum infection and Ixodes scapularis tick vector development. Sci Rep. 2018, 8(14224), 1-18.

Eszterbauer, et al. Molecular characterization of *Sphaerospora molnari* (Myzozoa), the agent of gill sphaerosporosis in common carp *Cyprinus carpio carpio*. Dis Aquat Organ, 2013, 104, 59-67.

Iniguez, et al. An α-Gal-containing neoglycoprotein-based vaccine partially protects against murine cutaneous eishmaniasis caused by Leishmania major. PLoS Negl Trop Dis. 2017, 11, e0006039, 1-25.

Kowalski, et al. Heterogeneity Among Isolates Reveals That Fitness in Low Oxygen Correlates With Aspergillus fumigatus virulence. mBio. 2016, 7(5), e01515-e01516, 1-13.

Korytar et al. A multicolour flow cytometry identifying defined leukocyte subsets of rainbow trout (*Oncorhynchus mykiss*). Fish Shellfish Immunol. 2013, 35, 2017-2019.

Korytar T, et al. The kinetics of cellular and humoral immune responses of common carp to presporogonic development of the myxozoan Sphaerospora molnari. Parasites Vectors, 2019, 12(208), 1-16.

Lanham and, Godfrey. Isolation of salivarian trypanosomes from man and other mammals using DEAE-cellulose. Exp Parasitol, 1970, 28, 521-534.

Reister et al. Complete genome sequence of the gram-negative probiotic *Escherichia coli* strain Nissle 1917. J Biotechnol, 2014, 187, 106-107.

Yilmaz, et al. Gut microbiota elicits a protective immune response against malaria transmission. Cell. 2014, 159, 1277-1289.

Soares et al. Microbiota Control of Malaria Transmission, Trends in Parasitology, 2016, 32(2), 120-130.

(Continued)

*Primary Examiner* — Jennifer E Graser

(74) *Attorney, Agent, or Firm* — Arrigo, Lee, Guttman & Mouta-Bellum LLP

(57) ABSTRACT

The present invention concerns an *E. coli* strains expressing high level of α-Gal, in particular selected in the group consisting of *E. coli* Nissle 1917 strain, *E. coli* O111 strain, *E. coli* O86:B7 strain, and mixture thereof, as a probiotic and/or feed additive and/or oral vaccine in a non-human animal, in particular fish and poultry, to prevent and/or reduce an infectious disease caused by a pathogen expressing α-Gal on its surface.

12 Claims, 9 Drawing Sheets

Specification includes a Sequence Listing.

(56) References Cited

PUBLICATIONS

Barth S et al. *Eschericha coli* Nissle 1917 for probiotic use in piglets: evidence for intestinal colonization. Journal of Applied Microbiology, 2009, 107(5), 1697-1710.
Saoud et al. Efficacy of Using an Allochtonous Probiotic Bacterium *Escherichia coli* Nissle (1917) on Growth and Immune Response of Nile Tilapia, World Aquaculture Society: Latin America and Caribbean Aquaculture 2019, Nov. 19-22, 2019, 1-2.
Cabezas Cruz et al. Control of vector-borne infectious diseases by human immunity against [alpha]-Gal. Expert Review of Vaccines, 2016, 15(8), 953-955.
Cabezas Cruz et al. Effect of blood type of anti-[alpha]-Gal immunity and the incidence of infectious diseases, Experimental & Molecular Medicine, 2017, 49(3), e301, 1-7.
Villarino et al. Composition of the gut microbiota modulates the severity of malaria, PNAS, 2016, 113(8), 2235-2240.
Kristian et al. Retargeting pre-existing human antibodies to a bacterial pathogen with an alpha-Gal conjugated aptamer, Journal of Molecular Med., 2015, 93(6), 619-631.
Mateos-Hernandez et al. Gut Microbia Abrogates Anti-[alpha]-Gal IgA Response in Lungs and Protects against Experimental Aspergillus Infection in Poultry, Vaccines, 2020, 8(2), 285, 2-21.

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Forward primer for amplification of GADPH gene of chicken or turkey

<400> SEQUENCE: 1
ccacatggca tccaaggagt 20

```
<210> SEQ ID NO 2
<211> LENGTH: 20
<212> TYPE: DNA
<213> ORGANISM: Artificial Sequence
<220> FEATURE:
<223> OTHER INFORMATION: Reverse primer for amplification of GADPH gene
      of chicken or turkey

<400> SEQUENCE: 2

ctccaacaaa gggtcctgct                                                20


<210> SEQ ID NO 3
<211> LENGTH: 21
<212> TYPE: DNA
<213> ORGANISM: Artificial Sequence
<220> FEATURE:
<223> OTHER INFORMATION: Forward primer for amplification of beta-actin
      gene of chicken or turkey

<400> SEQUENCE: 3

gagaaattgt gcgtgacatc a                                              21


<210> SEQ ID NO 4
<211> LENGTH: 19
<212> TYPE: DNA
<213> ORGANISM: Artificial Sequence
<220> FEATURE:
<223> OTHER INFORMATION: Reverse primer for amplification of beta-actin
      gene of chicken or turkey

<400> SEQUENCE: 4

cctgaacctc tcattgcca                                                 19


<210> SEQ ID NO 5
<211> LENGTH: 20
<212> TYPE: DNA
<213> ORGANISM: Artificial Sequence
<220> FEATURE:
<223> OTHER INFORMATION: Forward primer for amplification of IL-2 gene
      of chicken

<400> SEQUENCE: 5

ttggctgtat ttcggtagca                                                20


<210> SEQ ID NO 6
<211> LENGTH: 20
<212> TYPE: DNA
<213> ORGANISM: Artificial Sequence
<220> FEATURE:
<223> OTHER INFORMATION: Reverse primer for amplification of IL-2 gene
      of chicken

<400> SEQUENCE: 6

tcctgggtct cagttggtgt                                                20


<210> SEQ ID NO 7
<211> LENGTH: 20
<212> TYPE: DNA
<213> ORGANISM: Artificial Sequence
<220> FEATURE:
<223> OTHER INFORMATION: Forward primer for amplification of IL-2 gene
      of turkey

<400> SEQUENCE: 7

gagcatcgct atcaccagaa                                                20


<210> SEQ ID NO 8
```

<211> LENGTH: 20
<212> TYPE: DNA
<213> ORGANISM: Artificial Sequence
<220> FEATURE:
<223> OTHER INFORMATION: Reverse primer for amplification of IL-2 gene of turkey

<400> SEQUENCE: 8
gcagagtttg ctgactgcac 20

<210> SEQ ID NO 9
<211> LENGTH: 20
<212> TYPE: DNA
<213> ORGANISM: Artificial Sequence
<220> FEATURE:
<223> OTHER INFORMATION: Forward primer for amplification of IL-6 gene of chicken or turkey

<400> SEQUENCE: 9
agggccgttc gctatttgaa 20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for amplification of IL-6 gene of chicken or turkey

<400> SEQUENCE: 10
acggaacaac actgccatct 20

<210> SEQ ID NO 11
<211> LENGTH: 20
<212> TYPE: DNA
<213> ORGANISM: Artificial Sequence
<220> FEATURE:
<223> OTHER INFORMATION: Forward primer for amplification of IL-10 gene of turkey

<400> SEQUENCE: 11
gctgcgcttc tacacagatg 20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for amplification of IL-10 gene of turkey

<400> SEQUENCE: 12
tcccgttctc atccatcttc 20

<210> SEQ ID NO 13
<211> LENGTH: 20
<212> TYPE: DNA
<213> ORGANISM: Artificial Sequence
<220> FEATURE:
<223> OTHER INFORMATION: Forward primer for amplification of IL-4 gene of turkey

<400> SEQUENCE: 13
agagctcatt gcctccacac 20

<210> SEQ ID NO 14
<211> LENGTH: 20

<212> TYPE: DNA
<213> ORGANISM: Artificial Sequence
<220> FEATURE:
<223> OTHER INFORMATION: Reverse primer for amplification of IL-4 gene
of turkey

<400> SEQUENCE: 14
attgcaaggg acctgctctc 20

<210> SEQ ID NO 15
<211> LENGTH: 21
<212> TYPE: DNA
<213> ORGANISM: Artificial Sequence
<220> FEATURE:
<223> OTHER INFORMATION: Forward primer for amplification of MyD88 gene
of turkey

<400> SEQUENCE: 15
ttacgaagga agcagcagga g 21

<210> SEQ ID NO 16
<211> LENGTH: 20
<212> TYPE: DNA
<213> ORGANISM: Artificial Sequence
<220> FEATURE:
<223> OTHER INFORMATION: Reverse primer for amplification of MyD88 gene
of turkey

<400> SEQUENCE: 16
tggcaagaca tcccgatcaa 20

<210> SEQ ID NO 17
<211> LENGTH: 20
<212> TYPE: DNA
<213> ORGANISM: Artificial Sequence
<220> FEATURE:
<223> OTHER INFORMATION: Forward primer for amplification of IFN-gamma
gene of turkey

<400> SEQUENCE: 17
ctgaagaact ggacagagag 20

<210> SEQ ID NO 18
<211> LENGTH: 20
<212> TYPE: DNA
<213> ORGANISM: Artificial Sequence
<220> FEATURE:
<223> OTHER INFORMATION: Reverse primer for amplification of IFN-gamma
gene of turkey

<400> SEQUENCE: 18
caccagcttc tgtaagatgc 20

<210> SEQ ID NO 19
<211> LENGTH: 22
<212> TYPE: DNA
<213> ORGANISM: Artificial Sequence
<220> FEATURE:
<223> OTHER INFORMATION: Forward primer for amplification of 28S gene of
A.fumigatus

<400> SEQUENCE: 19
ctcggaatgt atcacctctc gg 22

<210> SEQ ID NO 20
<211> LENGTH: 17
<212> TYPE: DNA

-continued

```
<213> ORGANISM: Artificial Sequence
<220> FEATURE:
<223> OTHER INFORMATION: Reverse primer for amplification of 28S gene of
      A.fumigatus

<400> SEQUENCE: 20

tcctcggtcc aggcagg                                                17
```

USE OF *E. COLI* STRAINS EXPRESSING HIGH LEVEL OF α-GAL TO MODULATE IMMUNITY AND PROVIDE PROTECTION AGAINST INFECTIOUS DISEASES IN ANIMALS

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Mar. 27, 2023, is named 17999668_ST25.txt and is 5,265 bytes in size.

FIELD OF THE INVENTION

The present invention relates to the field of infectious diseases in non-human animals, in particular myxozoan parasitosis in fishes and aspergillosis in poultry.

BACKGROUND OF THE INVENTION

Infectious diseases constitute a major health problem for humans and non-human animals worldwide. Major infectious diseases, including malaria, tuberculosis, Lyme disease, anaplasmosis, myxozoan parasitosis and aspergillosis, are caused by some species of *Plasmodium, Mycobacterium, Borrelia, Anaplasma*, myxozoan parasites, and *Aspergillus*, respectively. Severe forms of these diseases can be lethal to both humans and non-human animals and produce considerable economical losses.

Aspergillosis, produced by the saprophytic opportunist fungus *Aspergillus fumigatus* with α-Gal on its surface is one of the most prevalent airborne fungal infection affecting humans and animals worldwide. *Aspergillus fumigatus* can cause a life-threatening disease in immunosuppressed and vulnerable individuals. Clinical presentation of aspergillosis varies according to the infectious load and the immunocompetence of the host. In animals, vulnerability to *Aspergillus* infection varies among host species, with birds exhibiting the highest susceptibility. Among galliform species, infected turkey poults show high morbidity and mortality rates. Clinical signs are usually unexpected and particularly severe, and mortality remains high even after antifungal treatment. Lung damage is commonly found in several forms of aspergillosis in birds.

*Sphaerospora molnari* is not a unique model but a representative for myxozoans in general (a highly diverse group of cnidarians with some 2600 species), which play an emerging role in fisheries and aquaculture, due to the effect of climate change (temperature) on their proliferation rate and occurrence. At present, there is no legalized treatment or vaccine for myxozoan pathogens in fish destined to human consumption.

In parallel, *Aspergillus fumigatus* is not a unique model but a representative, like *Sphaerospora molnari*, of a pathogen expressing α-Gal on the surface, and affecting poultry. Currently, there is not effective way to control and reduce severity of diseases caused by *S. molnari* (and other myxozoan pathogens) and *A. fumigatus* in fish and poultry, respectively. So there is still a need to develop a novel method to reduce myxozoan parasitosis in fisheries and aquaculture an aspergillosis in farmed chicken and turkey.

The inventors have demonstrated that the oral administration of *Escherichia coli* strains expressing high level of α-Gal, modulate the immunity in non-human animals such as fish and poultry infected by pathogen expressing α-Gal on their cell surface. In particular, they demonstrated that oral administration of *E. coli* Nissle 1917, hereafter referred as EC1917, in fishes (e.g. common carps), modulates the α-Gal immunity and was able to reduce the severity of sphaerosporosis affecting farmed fish. The inventors also demonstrated that oral administration of *Escherichia coli* O86:B7 strain, another bacterium expressing high level of α-Gal, protects turkeys against clinical aspergillosis and the formation of lung granulomas by reducing lung anti-α-Gal IgA to residual levels. Whereas these protective effects were not obtained with *E. coli* BL21, a bacterium expressing residual levels of α-Gal.

So the present invention describes *E. coli* strains expressing high level of α-Gal for use killed or alive as a probiotic and/or feed additive and/or oral vaccine to reduce the severity of infectious diseases affecting non-human animals, in particular farmed fish or poultry. Based on the fact that the mechanism of action is mediated by the modulation of the α-Gal immunity that can occur in all non-human animals lacking endogenous α-Gal (galactose-α-1,3-galactose), ie non-human animals that do not naturally produce α-Gal, this invention could be extended to all pathogens expressing α-Gal on their cell surface and other non-human hosts that do not naturally produce α-Gal. In craniates for example, the production of the carbohydrate α-Gal is mediated by the enzyme α-1,3-galactosyltransferase encoded by the gene ggta1 which appeared for the first time in the common ancestor of mammals. Inactivation of the gene ggta1 rendered old world monkeys, apes and humans unable to synthetize α-Gal. Lack of endogenous α-Gal allowed this group of primates to produce high antibody titers against α-Gal, an ability shared by non-mammalian craniates such as fish and birds.

And the modulation of anti-α-Gal immunity is critical for effective protection of animals against infectious agents. High levels of anti-gal Abs can be protective (for example, against malaria Cell. 2014; 159(6):1277-89), but also low levels of anti-gal Abs have been shown to be protective in other models (for example, depletion of inhibitory anti-α-Gal Abs in serum by a soluble trisaccharide-polylysine conjugate—commercial name RA-01, www.remabtx.com—protects patients from multidrug resistant bacteria Gram-negative bacteria (e.g. *Pseudomonas aeruginosa* and *Klebsiella pneumoniae*).

Surprisingly, the inventors demonstrated that the protective effect of *E. coli* O86:B7 was not associated with an increase in circulating anti-α-Gal IgY levels, but with a striking reduction of anti-α-Gal IgA in the lungs of infected turkeys. The same effect was observed with EC1917.

Thus, modulation of anti-α-Gal immunity in fish and poultry may protect these animals from several pathogens producing endogenous α-Gal.

SUMMARY OF THE INVENTION

A first object of the present invention is an *E. coli* strain expressing high level of α-Gal for use killed or alive as a probiotic and/or feed additive and/or oral vaccine in a non-human animal, in particular a non-mammalian craniate, to prevent and/or reduce an infectious disease caused by pathogens expressing α-Gal on its surface.

The present invention also concerns the *E. coli* strain expressing high level of α-Gal for use in a non-human animal that do not naturally produce α-Gal for promoting a protective anti-α-Gal immune response and/or promoting growth in non-human animal lacking α-Gal, and/or reducing inflammation or anemia in infected non-human animals.

Another object of the invention is a feed supplement for non-human animals that do not naturally produce α-Gal comprising, in a physiological medium, an efficient amount of *E. coli* strain expressing high level of α-Gal, in particular an efficient amount of *E. coli* strain selected in the group consisting of *E. coli* Nissle 1917 strain, *E. coli* O111 strain, *E. coli* O86:B7 strain, and mixture thereof.

Another object of the invention is an oral vaccine for non-human animals that do not produce α-Gal, in particular fish or poultry comprising, in a physiological medium, an inactivated or live attenuated *E. coli* strain expressing high level of α-Gal, in particular an efficient amount of *E. coli* strain selected in the group consisting of *E. coli* Nissle 1917 strain, *E. coli* O111 strain, *E. coli* O86:B7 strain, and mixture thereof.

Definitions

*Escherichia coli*, hereafter abbreviated as *E. coli* are incurred in numerous variants, which differ in the capsular antigens, surface antigens and flagella and can therefore be divided into numerous serological types.

The *E. coli* strains used in the present invention are strains expressing high level of α-Gal or having high α-Gal content.

The *E. coli* 'expressing high level of α-Gal' or 'having high α-Gal content' used according to the present invention may be selected by an in vitro method of detection of α-Gal glycan in *E. coli* strains and selection of the strains having high level of α-Gal.

The presence and level of α-Gal may be detected in *E. coli* strain by immunofluorescence and flow cytometry. Such method is illustrated in the examples for detection of α-Gal glycan in *A. fumigatus*.

In a particular embodiment, the *E. coli* 'expressing high level of α-Gal' or 'having high α-Gal content' used according to the present invention are selected according to the following protocol: *E. coli* cells were washed in PBS and then fixed and permeabilized with the Intracell fixation and permeabilization kit (Immunostep, Salamanca, Spain) following manufacturer recommendations. Fixed cells were incubated for 1 h at room temperature (RT) with 3% Human Serum Albumin (HSA, Sigma-Aldrich, MO, USA) in PBS. The monoclonal mouse anti-α-Gal antibody (mAb) M86 (Enzo Life Sciences, Farmingdale, N.Y.) diluted 1:50 in 3% HSA/PBS was used as primary Ab (incubation for 14 h at 4° C.) and the FITC-conjugated goat anti-mouse IgM (Abcam, Cambridge, UK) diluted 1:200 in 3% HSA/PBS as a secondary Ab (incubation for 1 h at RT). Detection of α-Gal by flow cytometry was performed as previously described (Cabezas-Cruz et al., 2018). Briefly, samples were analyzed on a FACSCalibur flow cytometer equipped with CellQuest Pro software (BD Bio-Sciences, Madrid, Spain). The cell population was gated according to forward-scatter and side-scatter parameters. The human promyelocytic leukemia HL60 cells, that do not express α-Gal, were included as a negative control. The mean and median fluorescence intensity (MFI) of *E. coli* cells (BL21, EC1917, O111, O86:B7, O128 and O113) was recorded and compared.

The said *E. coli* strains are disclosed hereunder.

The MFI values were measured according to the said method, as further illustrated in the examples and the obtained results were:

*E. coli* O86:B7 (MFI=552)—High α-Gal

*E. coli* Nissle EC1917 (MFI=1092 and 1536 in two experiments)—High α-Gal

*E. coli* O111 (MFI=1505)—High α-Gal

*E. coli* BL21 (MFI=346 and 128 in two experiments)—Low α-Gal

*E. coli* O128 (MFI=139)—Low α-Gal

*E. coli* O113 (MFI=131)—Low α-Gal

So an *E. coli* strain with 'high α-Gal content' or 'expressing high level of α-Gal' according to the present invention is a strain with MFI superior or equal to 500, preferably superior or equal to 530, more preferably superior or equal to 550, in particular according to the protocol as disclosed above.

In comparison, an *E. coli* strain with 'low α-Gal content' or 'expressing residual level of α-Gal' according to the present invention is a strain with MFI inferior or equal to 400, preferably inferior or equal to 380, more preferably inferior or equal to 350 in particular according to the protocol as disclosed above.

In a preferred embodiment, the *E. coli* strain is selected in the group consisting of *E. coli* Nissle 1917, *E. coli* O111, *E. coli* O86:B7 and mixture thereof.

These *E. coli* strains are well-known in the art.

In particular, the *E. coli* Nissle 1917 strain is referred in scientific publications as a non-pathogenic *E. coli* strain (serotype O6:K5:H1) having accession number DSM 6601 that was deposited under the terms of the Budapest Treaty on Jul. 11, 1991 in the German Collection for Microorganisms, DSMZ-Deutsche Sammlung von Mikrooganismen and Zellkulturen GmbH, located at Mascheroder Weg 1b, D-38124, Braunschweig, Germany (EP1636389). *E. coli* Nissle 1917 strain is also the active principle of a probiotic preparation (trade name Mutaflor(®)) commercialized by Ardeypharm and used for the treatment of patients with intestinal diseases such as ulcerative colitis and diarrhea. This strain is well characterized as its completed genome was sequenced (Reister et al., 2014).

The *E. coli* O86:B7 strain is an *E. coli* strain with serotype O86:K61(B7) available from the American Type Culture Collection (ATCC® 12701™; designation CDC6019-50; deposited name: *Escherichia coli* (Migula) Castellani and Chalmers).

The *E. coli* O111 strain is an *E. coli* strain with serotype O111:K58(B4):H—acquired from the American Type Culture Collection (ATCC® 33780™; designation Stoke W; deposited name: *Escherichia coli* (Migula) Castellani and Chalmers.

The *E. coli* O128 strain (Cigleris), which is not of interest for the invention, is an *E. coli* strain with serotype O128:H2 having accession number DSM 8703 that was deposited under the terms of the Budapest Treaty before 12.1.1993 in the German Collection for Microorganisms, DSMZ-Deutsche Sammlung von Mikrooganismen and Zellkulturen GmbH, located at Mascheroder Weg 1b, D-38124, Braunschweig, Germany. Its name is *Escherichia coli* (Migula 1895) Castellani and Chalmers 1919. This strain is also referred in scientific publications Oerskov, I. (1977). Serology, chemistry, and genetics of O and K antigens of *Escherichia coli*. Bacteriol. Rev. 41: 667-710 and Beutin, L. (1990). Die Bedeutung and Erkennung von *Escherichia coli* als Krankheitserreger beim Menschen. *Bundesgesundheitsblatt* 9: 380-386. (https://www.dsmz.de/collection/catalogue/details/culture/DSM-8703).

The *E. coli* O113 strain, which is not of interest for the invention, is an *E. coli* strain with serotype O113:H21—acquired from the American Type Culture Collection (ATCC® BAA-176™; designation: CDC 2001-3004; deposited name: *Escherichia coli* (Migula) Castellani and Chalmers.

The *E. coli* strains according to the invention are used as alive, inactivated or dead forms (also named 'killed').

In a particular embodiment, the *E. coli* strains are used killed (inactivated) or alive.

They can be used in the form of active fractions of cellular components or metabolites. The *E. coli* strains or their active fractions can also be used in the form of a lyophilized powder, a culture supernatant and/or, where appropriate, in a concentrated form.

In a particular embodiment, the *E. coli* strains are killed or alive and used as a probiotic and/or feed additive and/or oral vaccine.

The term 'probiotic' refers to live non-pathogenic micro-organism, e.g., a bacterium, which can confer health benefits to a host organism, generally by improving or restoring the gut flora. In the context of the present invention, the *E. coli* strains having high α-Gal content, in particular selected from *E. coli* Nissle 1917, *E. coli* O111 and *E. coli* O86:B7, provide protection against infectious diseases in comparison to other strains having low level α-Gal content such as *E. coli* BL21, O128 and O113 as illustrated by the further examples. And *E. coli* Nissle 1917 strain even promotes fish immunity and growth in comparison *E. coli* BL21, as shown in FIG. 1.

The term 'oral vaccine' is a biological preparation which is administered in needle-free and oral manner, that provides active acquired immunity to a particular infectious disease.

The three principal vaccines types are: inactivated vaccines (whole cells killed bacteria and fractional inactivated vaccine), live attenuated vaccine and DNA-based vaccine.

The term 'feed additive' can also be distinguished from 'probiotic' and 'oral vaccines' in a way that 'probiotics' are alive microbes and feed additive do not need to be alive and/or induce 'active acquired immunity'.

The *E. coli* strains having high α-Gal content play a role of immunomodulator. The term 'immunomodulator' according to the invention means that the *E. coli* strains having high α-Gal content, in particular selected from *E. coli* Nissle 1917, *E. coli* O111 and *E. coli* O86:B7, are able to modulate the α-Gal immunity. This modulation may include differential changes in the levels of anti-gal Abs in different tissues and/or changes in the levels of several cytokines in different tissues.

The term 'myxozoans' in the invention refers to a class of aquatic parasitic cnidarian animals, including two sub-classes: Malacosporea and Myxosporea. Over 1300 species have been described and many have a two-host lifecycle, involving a fish and an annelid worm or a bryozoan. Myxozoans can live in both freshwater and marine habitats. Infection occurs through valved spores. Each of these contains one or two sporoblast cells and one or more polar capsules that contain filaments which anchor the spore to its host. The sporoblasts are then released as a motile form, called an amoebula, which penetrates the host tissues and develops into one or more multinucleate plasmodia. Certain nuclei later pair up, one engulfing another, to form new spores.

Relationships between myxosporeans and their hosts are often highly evolved and those do not usually result in severe diseases of the natural host. Infection in fish hosts can be extremely long-lasting, potentially persisting for the lifetime of the host. However, an increasing number of myxosporeans have become commercially important pathogens of fish, largely as a result of aquaculture bringing new species into contact with myxosporeans to which they had not been previously exposed and to which they are highly susceptible. The economic impact of such parasites can be severe, especially where prevalence rates are high; they may also have a severe impact on wild fish stocks.

In particular, the table 1 hereunder provides a non-limitative list of myxozoans and targeted fishes they may infect.

TABLE 1

| Myxozoans (parasites) | Fishes |
|---|---|
| *Sphaerospora molnari* | *Cyprinus carpio* |
| *Enteromyxum leei* | *Sparus aurata* |
| *Tetracapsuloides bryosalmonae* | Salmonidae (family) |
| *Myxobolus cerebralis* | Salmonidae (family) |
| *Ceratonova shasta* | Salmonidae (family) |

By 'preventing and/or reducing infectious diseases' or 'preventing and/or reducing the severity of infectious diseases', it means preventing and/or reducing the levels of the infectious agent (pathogen), the pathological lesions including granulomas and inflammation induced by the infection.

The term 'feed' encompasses edible materials(s) which are consumed by animals and contribute energy and/or nutrients to the animals' diet.

By 'feed supplement' according to the invention, it means a feed used with another to improve the nutritive balance or performance of the total and intended to be: (i) fed undiluted as a supplement to other feeds; or (ii) offered free choice with other parts of the ration separately available; or (iii) further diluted and mixed to produce a complete feed.

A 'complete feed' is a nutritionally adequate feed for animals other than man: by specific formula is compounded to be fed as the sole ration and is capable of maintaining life and/or promoting production without any additional substance being consumed except water.

A 'compound feed' is a mixture of products of vegetable or animal origin in their natural state, fresh or preserved, or products derived from the industrial processing thereof, or organic or inorganic substances, whether or not containing additives, for oral feeding in the form of a complete feed.

A 'feed composition' is a composition to be fed by non-human animals.

in peripheral blood. Oral administration of EC1917 decreased the level of anti-α-Gal IgM in sera after infection with *S. molnari* (D). Anti-α-Gal Ab reactivity in sera was tested by indirect ELISA against Galα1-3Gal-HSA. Results were compared by Student's t-test with unequal variance (*$p<0.05$; n=5/group, one biological replicate). Results shown are the means and standard deviations.

Figure 3:
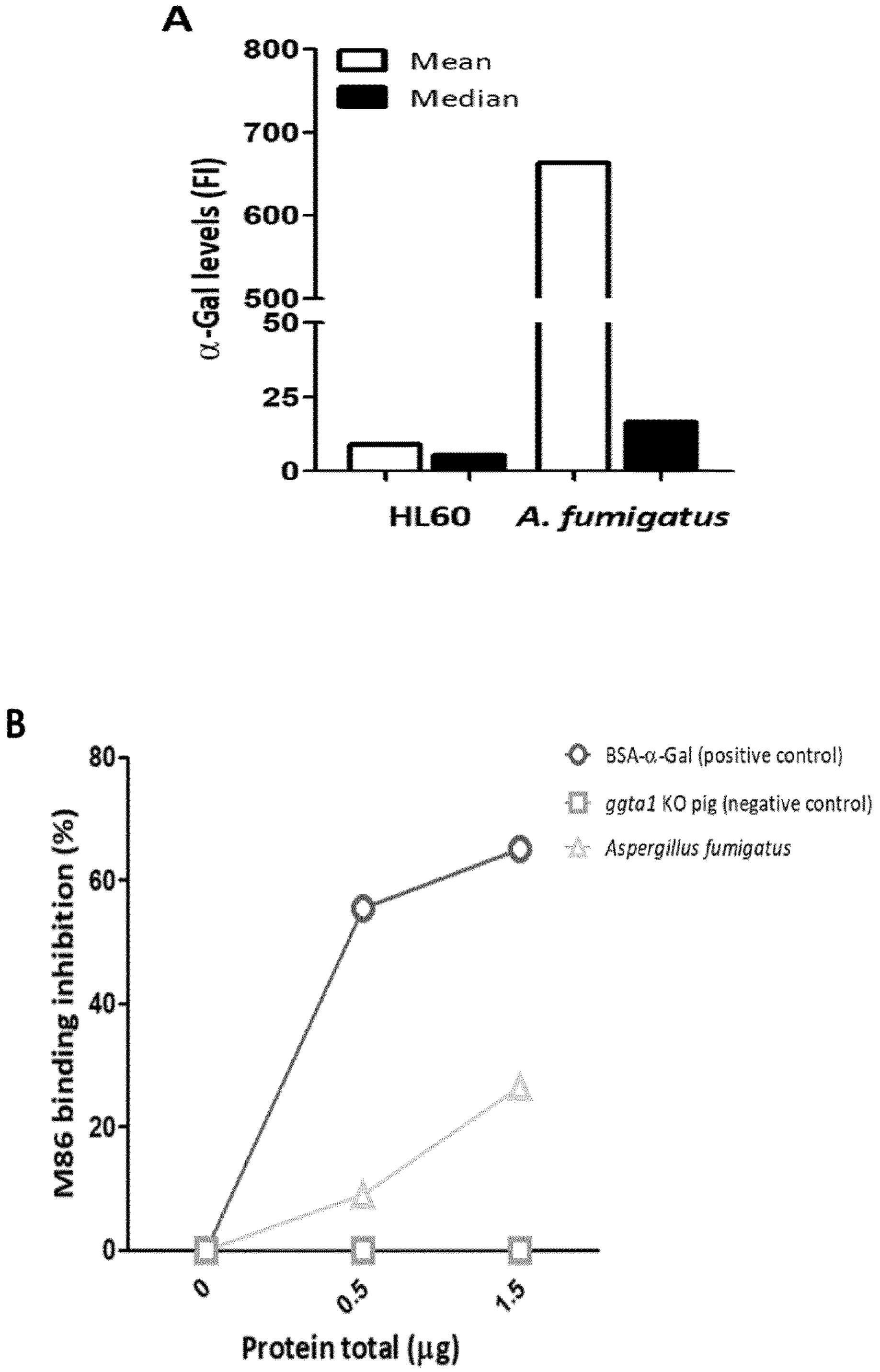

FIG. 3. Detection of α-Gal in *A. fumigatus*. α-Gal expression in conidia surface was measured by flow cytometry using M86 and Goat anti-mouse IgM-FITC. Mean and median fluorescence intensity (FI) values are presented. Human HL60 cells served as a negative control (A). The association of α-Gal to fungal proteins was assessed by an inhibition ELISA (B).

Figure 4:
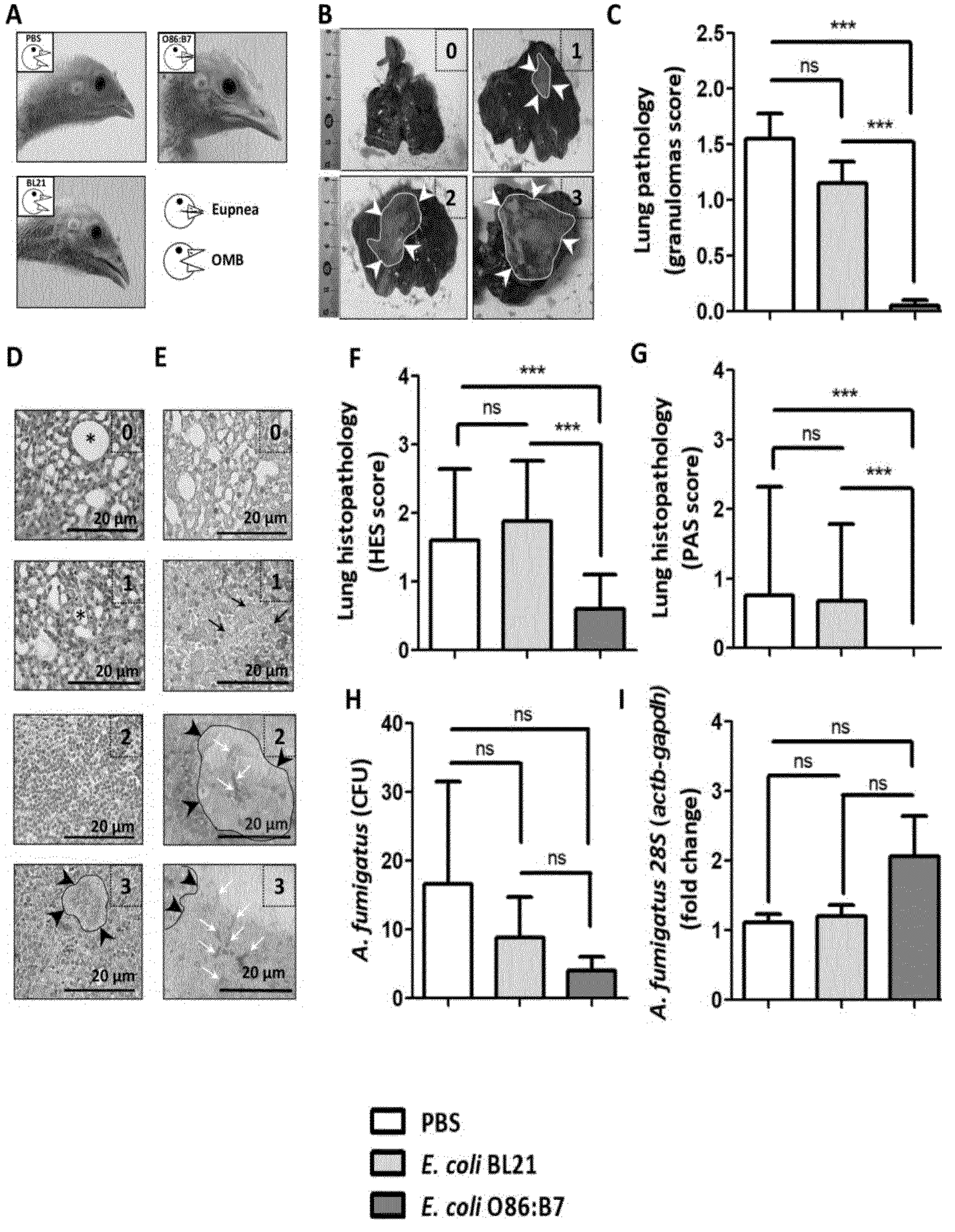

FIG. 4. Oral administration of *E. coli* O86:67 protects turkeys against aspergillosis. Clinical examination revealed that *A. fumigatus* infection produces open-mouthed breathing (OMB) in turkeys treated with PBS or *E. coli* BL21. Turkeys treated with *E. coli* O86:B7 were protected from developing OMB (A). Pulmonary lesions (i.e. granulomas, delimited area and white arrow heads) were scored (see methods). Examples of lungs with scores 0 to 3 are shown (B). Granuloma score was lower in turkeys treated with *E. coli* O86:B7 (C). Lung samples were processed for histopathology and stained with hematoxylin-eosin-saffron (HES, D) and periodic acid-schiff (PAS, E). Histological lesions were scored (see methods). Examples of histopathology samples with scores 0 to 3 are shown. Visible peribronchial regions (asterisk) and granulomas (delimited area and black arrow heads) are shown (HES score, D). The presence of fungal germ-tube/hyphae (black arrows) and mycelium (white arrows) was scored (see methods). Granulomas associated with fungal hyphae (delimited area and black arrow heads) are shown (PAS score, E). HES and PAS scores were lower in turkeys treated with *E. coli* O86:B7 (F and G). The presence of viable *Aspergillus* in lungs was quantified by colony-forming unit (CFU) counting assay (H). Fungal DNA levels were measured by *A. fumigatus*-specific 28S qPCR normalizing against turkey actb and gapdh as host genes using the $2^{-\Delta\Delta Ct}$ ratio method. Results are relative to 28S levels in the control group (i.e. PBS) (I). No significant change was observed in the amount of CFU and 28S fold change (H and I). Size of bars is indicated. 100× magnification. Results shown are means and standard deviation values. Results were compared by One-way ANOVA with Dunnett's multiple comparison test applied for individual comparisons (***$p<0.0001$; 2 experiments, n=30).

Figure 5:
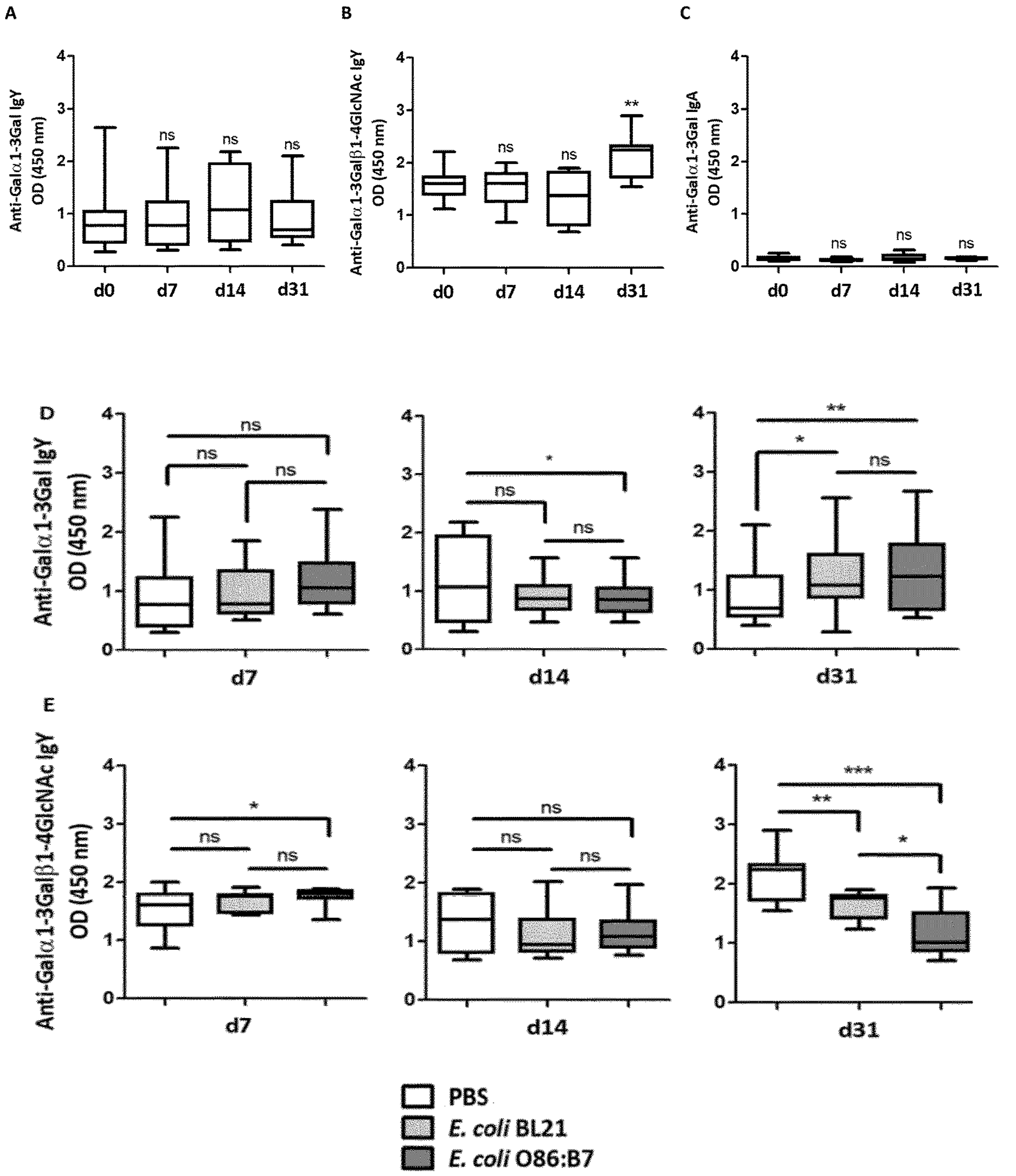

FIG. 5. Oral administration of *E. coli* O86:657 induces a significant decrease in the levels of anti-Galα1-3Galβ1-4GlcNAc IgY Abs in *A. fumigatus*-infected turkeys.

Levels of circulating IgY against Galα1-3Gal (A), circulating IgY against Galα1-3Galβ1-4GlcNAc (B) and circulating IgA against Galα1-3Gal (C) were measured by indirect ELISA in control turkeys treated with PBS.

The levels of circulating anti-α-Gal IgY Abs to Galα1-3Gal (D) and Galα1-3Galβ1-4GlcNAc (E) were measured by ELISA. Anti-Galα1-3Gal IgY Abs increased in the sera of turkeys treated with *E. coli* O86:B7 and *E. coli* BL21. Oral administration of *E. coli* O86:B7 produces a significant reduction in anti-Galα1-3Galβ1-4GlcNAc IgY Abs when compared with turkeys that were treated or not *E. coli* BL21. Results shown are means and standard deviation values. Results were compared by One-way ANOVA with Dunnett's multiple comparison test applied for individual comparisons (*$p<0.05$, $p<0.001$, *$p<0.0001$; 2 experiments, n=30 and three technical replicates per sample).

Figure 6:
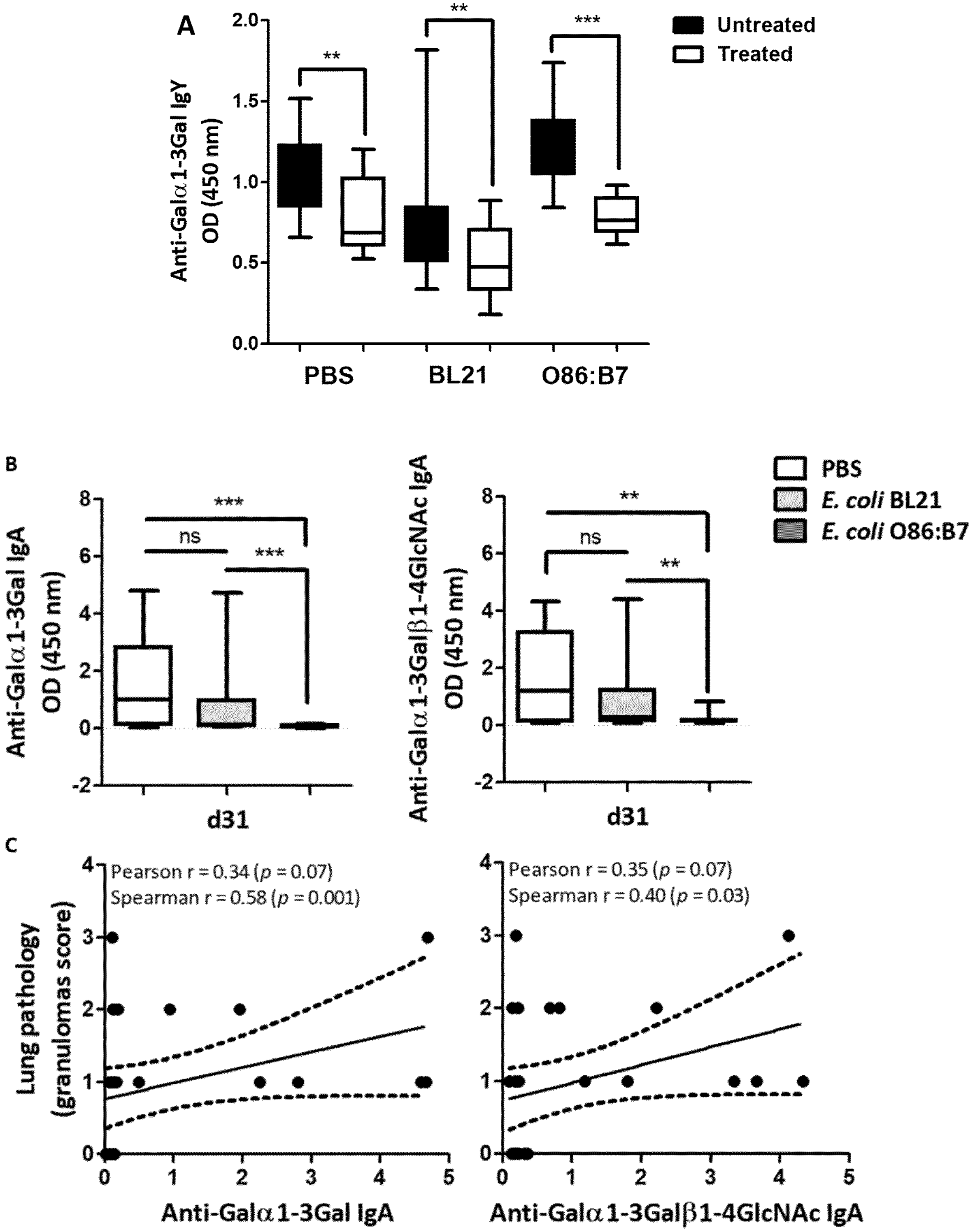

FIG. 6. Oral administration of *E. coli* O86:67 decreases the levels of anti-α-Gal IgA Abs which correlate with lung pathology in *A. fumigatus*-infected turkeys.

The specificity of turkey anti-α-Gal Abs was tested by indirect ELISA in animals treated with PBS, *E. coli* BL21 and *E. coli* O86:B7. In comparison with the untreated group, a reduction in reactivity against Galα1-3Gal-HSA was observed after the antigen was pretreated with α-galactosidase (A).

The levels of IgA against α-Gal, Galα1-3Gal and Galα1-3Galβ1-4GlcNAc in lungs of *A. fumigatus*-infected turkeys were measured by ELISA. The levels of anti-α-Gal IgA between groups were compared by one-way ANOVA with Dunnett's multiple comparison test applied for individual comparisons ($p<0.001$, *$p<0.0001$; 2 experiments, n=30 and three technical replicates per sample) (B). Correlation between the levels of anti-Galα1-3Gal and anti-Galα1-3Galβ1-4GlcNAc IgA and granuloma scores of turkeys treated with PBS, *E. coli* O86:B7 and *E. coli* BL21. Pearson and Spearman coefficients rand p values are indicated (C).

Figure 7:
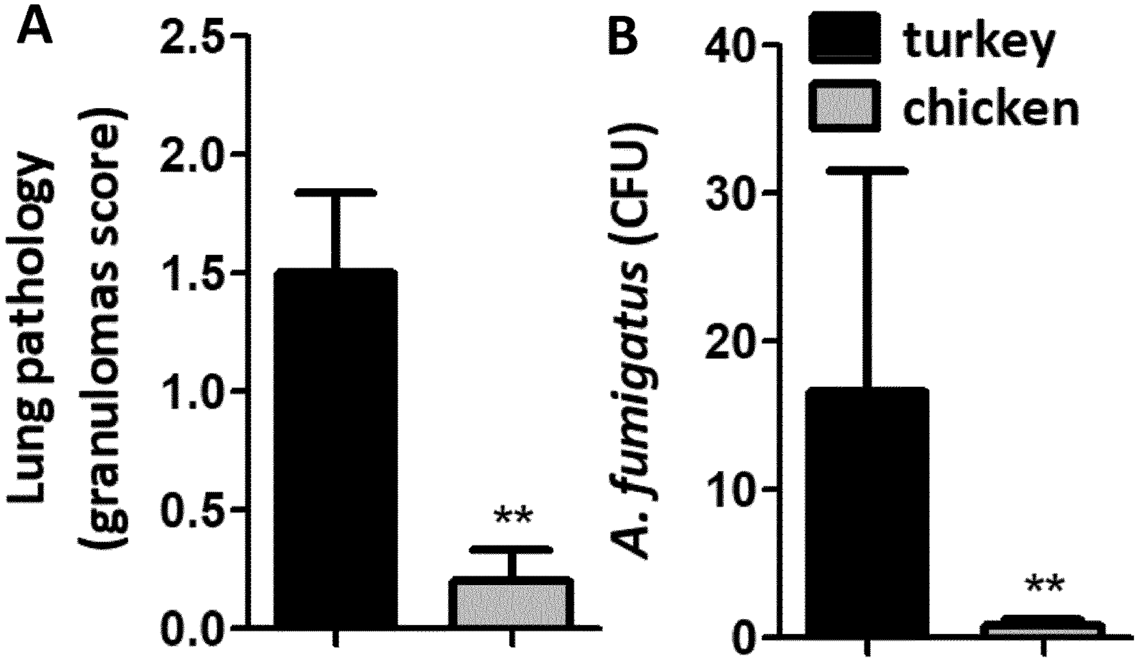

FIG. 7. Granuloma score and CFU in turkeys and chickens infected with *A. fumigatus*. Lung granuloma score (A) and CFU counting (B) was lower in chicken than in turkeys (A). Results shown are means and standard deviation values. Results were compared by Mann-Whitney U test (**$p<0.001$; 1 experiment with chickens, n=5 and 2 experiments with turkeys, n=10).

Figure 8:
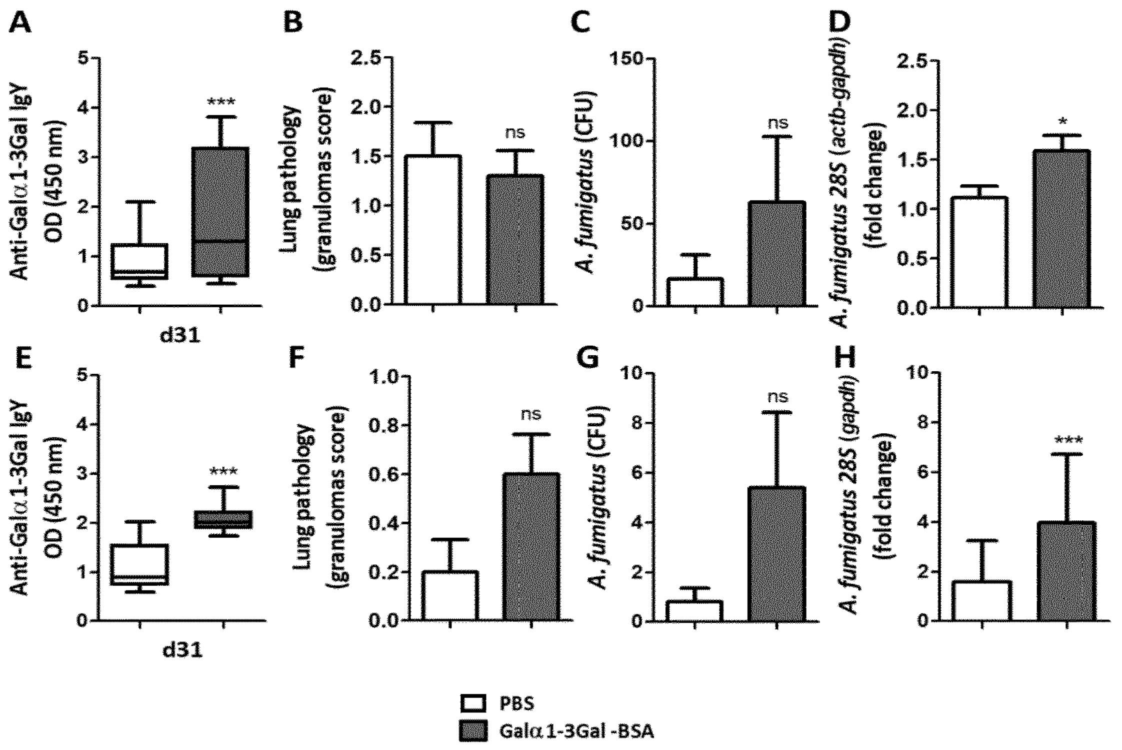

FIG. 8. Immunization against α-Gal-BSA increases fungal burden in turkeys and chickens. The levels of circulating anti-α-Gal IgY Abs to Galα1-3Gal, lung granuloma score and *A. fumigatus* CFU number and 28S levels in lungs, were quantified in turkeys (A, B, C and D) and chickens (E, F, G and H). Immunization against α-Gal-BSA increases the levels of anti-α-Gal IgY Abs to Galα1-3Gal and *A. fumigatus* 28S levels in turkeys (A and D) and chicken (E and H). Results shown are means and standard deviation values. Results were compared by unpaired non-parametric Mann Whitney's test (*$p<0.0001$, ***$p<0.0001$; 1 experiment with chicken, n=10 and 2 experiments with turkeys, n=20 and three technical replicates per sample in the ELISA (A) and (B) and qPCR (D) and (H) assays).

Figure 9:
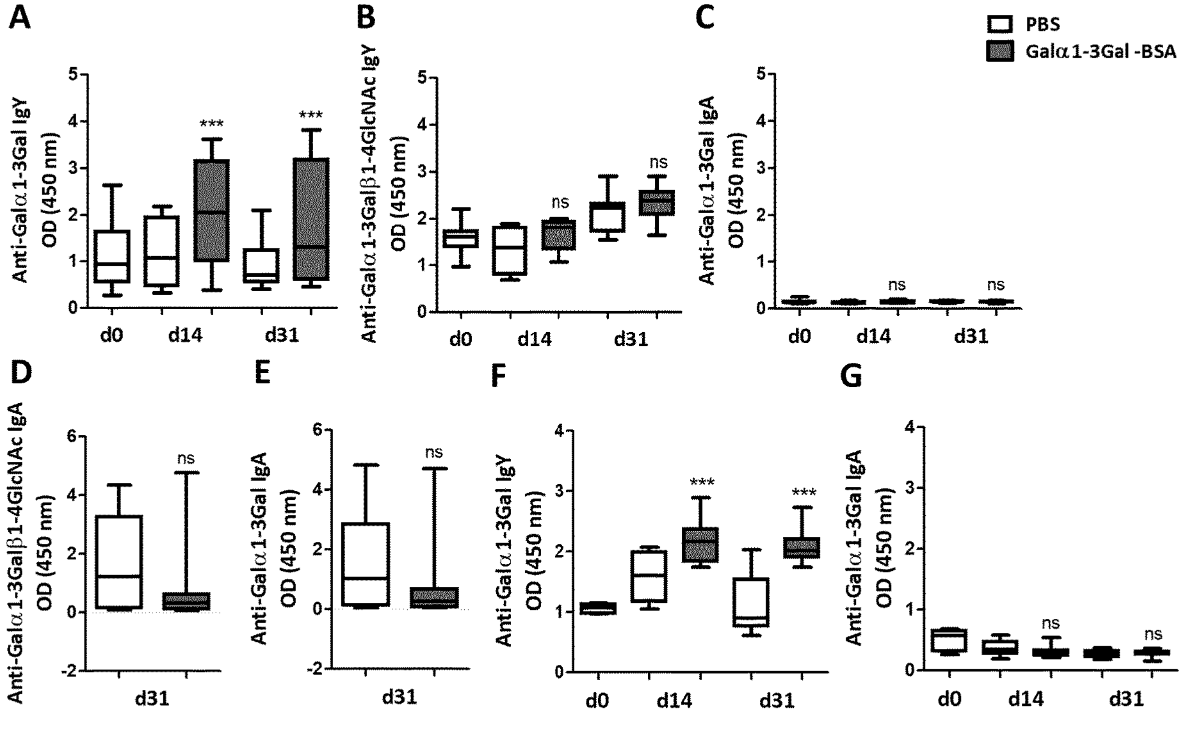

FIG. 9. Levels of circulating IgY against Galα1-3Gal (A), circulating IgY against Galα1-3Galβ1-4GlcNAc (B) and circulating IgA against Galα1-3Gal (C) were measured in turkey sera by indirect ELISA in animals immunized with α-Gal-BSA (Galα1-3Gal-BSA) or the mock vaccine (PBS). Levels of IgA against Galα1-3Gal (D), and Galα1-3Galβ1-4GlcNAc (E) were measured in turkey lungs. Levels of circulating IgY (F) and circulating IgA (G) against Galα1-3Gal were measured by indirect ELISA in sera of chickens immunized with α-Gal-BSA (Galα1-3Gal-BSA) or the mock vaccine (PBS).

Figure 10:
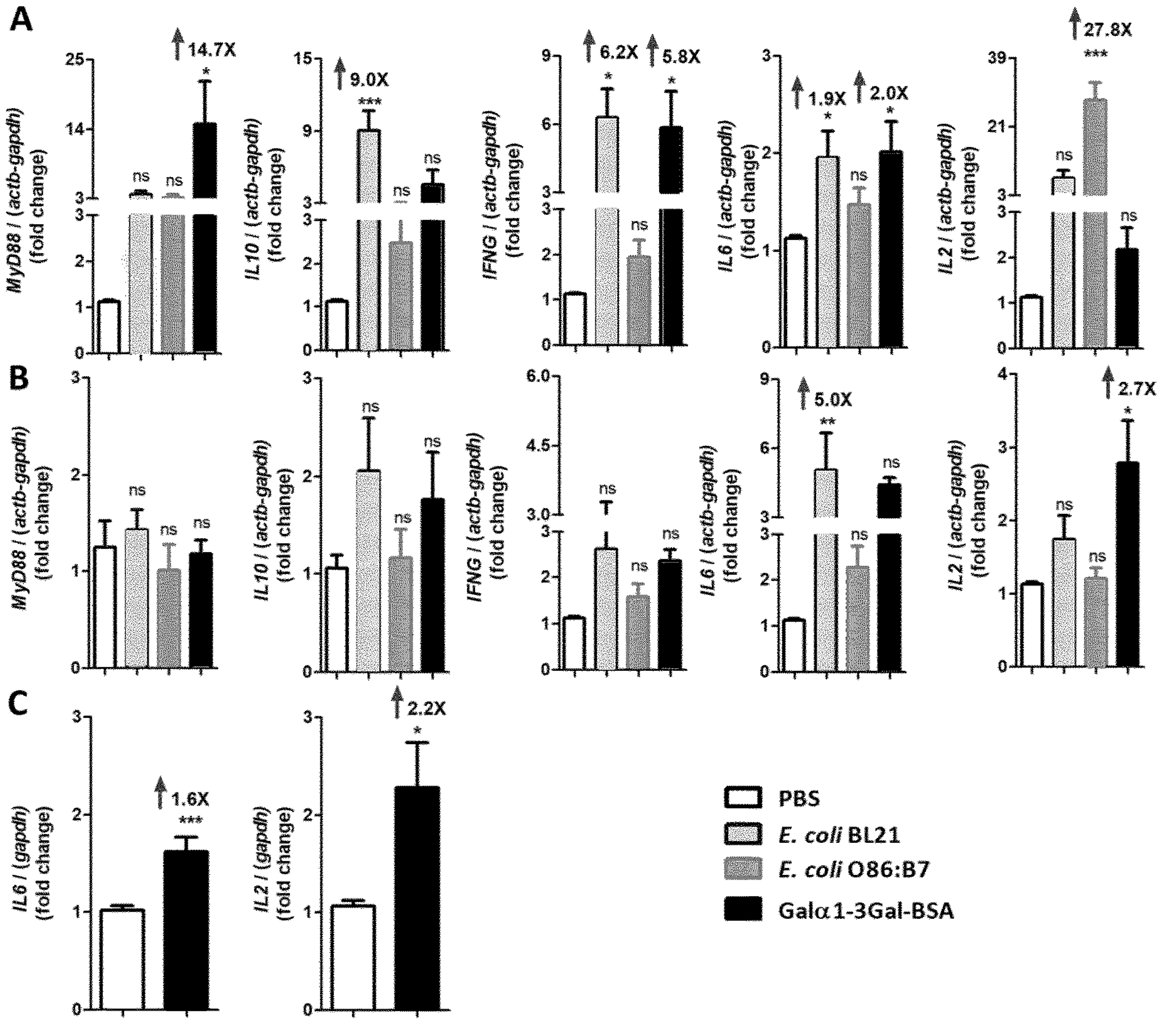

FIG. 10. Expression of turkey and chicken cytokine genes in response to oral administration of *E. coli* O86:67 and *E. coli* BL21 and α-Gal-BSA immunization. The figure displays the mRNA expression levels of INFγ, IL6, IL2, IL10 and MyD88 in ceca (A) and lungs (B) of turkeys and IL6 and IL2 in lungs of chicken (C). Total RNA was extracted and gene expression levels were measured by qPCR normalizing against turkey actb and gapdh as housekeeping genes using the using the $2^{-\Delta\Delta Ct}$ ratio method. Expression levels are relative to the control group (i.e. PBS). Results shown are means and standard deviation values. Results were compared by One-way ANOVA with Dunnett's multiple comparison test applied for individual comparisons (*$p<0.0001$,

***p<0.0001; 1 experiment with chicken, n=10 and 2 experiments with turkeys, n=40 and three technical replicates per sample).

DETAILED DESCRIPTION OF EMBODIMENTS OF THE INVENTION

The present invention concerns an *E. coli* strain expressing high level of α-Gal, in particular selected in the group consisting of *E. coli* Nissle 1917 strain, *E. coli* O111 strain, *E. coli* O86:B7 strain and mixtures thereof, for use killed or alive as a probiotic and/or feed additive and/or oral vaccine in a non-human animal to prevent and/or reduce an infectious disease caused by a pathogen expressing α-Gal on its surface.

Non-Human Animals Lacking Endogenous α-Gal

The non-human animal according to the invention is selected in the group consisting of non-human animals that do not produce α-Gal, meaning they do not naturally produce α-Gal, to be distinguished to animals that may be genetically modified to not produce α-Gal.

The said non-human animals that do not produce naturally α-Gal may be identified by well-known methods. In particular, the presence of α-Gal in protein extracts or cell surface can be measured by inhibition ELISA and flow cytometry using the anti-α-Gal-specific monoclonal Ab (mAb) M86 (Enzo Life Sciences Inc.) and the lectins from *Marasmius oreades* (MOA) and *Bandeiraea simplicifolia* (BS-I Isolectin B4, Sigma Aldrich) or collected from the literature.

In a particular embodiment, the non-human animal is selected in the group consisting of birds and fishes.

The birds belong to Passeriformes, Anseriformes or Galiformes, in particular from the species, *Pica pica, Gallus* sp. (chicken) *M. gallopavo* (turkey).

For birds in the present invention, we also referred to poultry including chicken and turkey.

The fishes belong to fishes for aquaculture, preferably carps, see bream, salmon, trout, tilapia, and catfish, or tropical fishes in the aquarium.

In particular, the fishes belong to Cypriniformes, in particular Freshwater fish, such as *Cyprinus carpio* (common carp), *Danio rerio* (zebra fish), *Carassius* sp.

In a particular and preferred embodiment, the non-human animals of interest are non-human animals destined to human consumption.

In a particular and preferred embodiment, the non-human animal is fish.

In a particular embodiment, the fish is a tropical fish in the aquarium.

And preferably, the fish is selected in the group consisting of fishes for aquaculture, preferably selected from carps, see bream, salmon, trout, tilapia, and catfish.

In a particular and preferred embodiment, the non-human animal is poultry, in particular chicken or turkey, preferably turkey.

Pathogen Expressing α-Gal on its Surface

The present invention concerns in particular the aspergillosis affecting poultry and myxozoan parasitosis affecting farmed fish.

*Aspergillus*

Aspergillosis is a non-contagious respiratory disease caused by a fungal species known as *Aspergillus*. In decreasing order of incidence, spores produced by *A. fumigatus, A. flavus, A. niger, A. glaucus* and *A. terreus* are infective to poultry.

Aspergillosis affects chickens, ducks, turkeys, waterfowl, game birds, and many other bird species. Young birds are the most susceptible to infection, though older birds under stress or with compromised immune systems can develop chronic Aspergillosis.

In addition, vulnerability to this fungal infection varies among bird species, with turkeys having the highest susceptibility when compared to chickens.

There is no known treatment for Aspergillosis in infected birds, so prevention is key to controlling the disease and protecting flocks.

So in a particular embodiment, the pathogen expressing α-Gal on its surface and infecting poultry is an *Aspergillus*, preferably *Aspergillus fumigatus.*

So in a particular embodiment of the invention, the non-human animal is a poultry, in particular selected in the group consisting of farmed turkey or chicken.

In particular, the pathogen expressing α-Gal on its surface and infecting poultry is an *Aspergillus*, preferably *Aspergillus fumigatus.*

So in a particular and preferred embodiment, *E. coli* strain is used killed or alive as probiotic and/or feed additive and/or oral vaccine to prevent and/or reduce aspergillosis in poultry, in particular farmed turkey or chicken, caused by *Aspergillus fumigatus.*

In particular, *E. coli* strain is used killed or alive in non-human animals as a probiotic and/or feed additive and/or oral vaccine for promoting a protective anti-α-Gal immune response in non-human animal lacking α-Gal, and/or reducing inflammation or anemia in infected non-human animals.

Myxozoan

In another and particular embodiment, the pathogen expressing α-Gal on its surface and infecting fishes is a myxozoan.

Myxozoan according to the invention is defined as disclosed above.

In a particular embodiment, the myxozoan is selected in the group consisting of *Sphaerospora molnari* infecting *Cyprinus carpio, Enteromyxum leei* infecting *Sparus aurata*, or *Tetracapsuloides bryosalmonae, Myxobolus cerebralis* or *Ceratonova Shasta* infecting Salmonidae.

In a preferred embodiment of the invention, *E. coli* strain is used killed or alive as a probiotic and/or feed additive and/or oral vaccine to prevent and/or reduce sphaerosporosis in common carp, in particular in *Cyprinus carpio*, caused by *Sphaerospora molnari.*

In a particular embodiment, *E. coli* strain is used killed or alive in non-human animals as a probiotic and/or feed additive and/or oral vaccine for promoting a protective anti-α-Gal immune response and growth in non-human animal lacking α-Gal, and/or reducing inflammation or anemia in infected non-human animals.

In a particular embodiment, *E. coli* strain is E Coil Nissle 1917 strain.

In another particular embodiment, *E. coli* strain is *E. coli* O86:B7 strain.

In another particular embodiment, *E. coli* strain is *E. coli* O111 strain.

In a particular embodiment, the *E. coli* strain is *E. coli* Nissle 1917, in particular for use killed or alive as probiotic and/or feed additive and/or oral vaccine to prevent and/or reduce sphaerosporosis in common carp, in particular in *Cyprinus carpio*, caused by *Sphaerospora molnari.*

In a particular embodiment, the *E. coli* strain is *E. coli* O111, in particular for use killed or alive as probiotic and/or feed additive and/or oral vaccine to prevent and/or reduce sphaerosporosis in common carp, in particular in *Cyprinus carpio*, caused by *Sphaerospora molnari*.

In a particular embodiment, the *E. coli* strain is *E. coli* O86:B7, in particular for use killed or alive as probiotic and/or feed additive and/or oral vaccine to prevent and/or reduce aspergillosis in poultry, in particular farmed turkey or chicken, caused by *Aspergillus fumigatus*.

In a particular embodiment, the *E. coli* strain is *E. coli* O111, in particular for use killed or alive as probiotic and/or feed additive and/or oral vaccine to prevent and/or reduce sphaerosporosis in common carp, in particular in *Cyprinus carpio*, caused by *Sphaerospora molnari*.

In a particular embodiment, the *E. coli* strain of the present invention, preferably the *E. coli* O86:B7 strain, decreases proinflammatory anti α-Gal IgA to residual levels in the lungs of non-human animals infected with pathogens expressing α-Gal.

In particular, the *E. coli* strain, preferably the *E. coli* O86:B7 strain, induces residual levels anti α-Gal IgA and reduces lung lesions (e.g. granulomas) and inflammation.

Use as Feed Composition or Supplement (Feed Additive)

An *E. coli* strain having high α-Gal content as defined in the invention, is used as feed supplement or additive.

In a particular embodiment, *E. Coli* Nissle 1917 is used as a feed supplement.

In another particular embodiment, *E. coli* O86:B7 strain is used as a feed supplement.

In another particular embodiment, *E. coli* O111 strain is used as a feed supplement.

A feed supplement according to the invention is defined as disclosed above.

The present invention also relates to a feed supplement for non-human animals that do not produce α-Gal comprising, in a physiological medium, an efficient amount of *E. coli* strain having high α-Gal content, in particular an efficient amount of *E. coli* strain selected in the group of *E. coli* Nissle 1917, *E. coli* O111 strain, *E. coli* O86:B7 strain and mixture thereof.

By 'efficient amount' of strain having high α-Gal content, it means an amount of *E. coli* strain having high α-Gal content able to modulate α-Gal immunity and provide protection against infectious diseases in animals. The man skilled in the art will adapt the said efficient amount of *E. coli* Nissle 1917, *E. coli* O111 or *E. coli* O86:B7 strain depending the type of non-human animal to be treated, the type of pathogen and the type of feed supplement.

The efficient amount of *E. coli* Nissle 1917 will generally range from $1\times10^7$ CFU to $1\times10^{10}$ CFU (Colony-Forming Unit) per dose per animal, in particular from $1\times10^7$ CFU to $5\times10^9$ CFU per dose per animal, in particular from $1\times10^8$ CFU to $5\times10^9$ CFU per dose per animal. In a particular embodiment, the feed supplement may contain a number of colony forming units of *E. coli* Nissle 1917 ranging from $5\times10^8$ CFU to $5\times10^9$ CFU per dose per animal, in particular for fish.

The efficient amount of *E. coli* O86:B7 strain will generally range from $1\times10^7$ CFU to $1\times10^{10}$ CFU (Colony-Forming Unit), in particular from $1\times10^7$ CFU to $5\times10^9$ per dose per animal, in particular from $1\times10^8$ CFU to $5\times10^9$ CFU per dose per animal. In a particular embodiment, the feed supplement may contain a number of colony forming units of *E. coli* O86:B7 ranging from $5\times10^8$ CFU to $5\times10^9$ CFU per dose per animal, in particular for poultry.

The efficient amount of *E. coli* O111 will generally range from $1\times10^7$ CFU to $1\times10^{10}$ CFU (Colony-Forming Unit), in particular from $1\times10^7$ CFU to $5\times10^9$ per dose per animal, in particular from $1\times10^8$ CFU to $5\times10^9$ CFU per dose per animal. In a particular embodiment, the feed supplement may contain a number of colony forming units of *E. coli* O111 ranging from $5\times10^8$ CFU to $5\times10^9$ CFU per dose per animal, in particular for fish or poultry.

In a particular and preferred embodiment, the oral administration is a continuous administration of doses as disclosed above, for several days, in particular for 8 to 16 days, in particular 12 days. As an example, the administration comprises 3 consecutive administrations (~$10^9$ CFU) of *E. coli* strain expressing high level of α-Gal repeated 3 times at 4 days intervals. Such continuous administration of large doses of highly α-Gal expressing *E. coli* strain decreased or totally abrogated responsiveness to the α-Gal on the surface of the said pathogen, when present in the lungs.

So in a particular embodiment, the feed supplement is for use in a continuous oral administration in fish or poultry, in particular for 8 to 16 days, and wherein the efficient amount ranges from $1\times10^7$ CFU to $1\times10^{10}$ CFU (Colony-Forming Unit), in particular from $1\times10^8$ CFU to $5\times10^9$ CFU per dose per animal.

The feed supplement may be on liquid or solid form adapted for oral administration to non-human animals, in particular to farmed poultry or fish.

The man skilled in the art will develop feed supplements according to his knowledge in feeding such non-human animals, in particular fish and poultry.

Use as Oral Vaccine

An *E. coli* strain having high α-Gal content as defined in the invention, is used as oral vaccine.

In a particular embodiment, *E. coli* Nissle 1917 is used as oral vaccine.

In another particular embodiment, *E. coli* O86:B7 strain is used as oral vaccine.

In another particular embodiment, *E. coli* O111 strain is used as oral vaccine.

An oral vaccine according to the invention is defined as disclosed above.

So, another object of the invention is an oral vaccine for non-human animals that do not produce α-Gal, in particular fish or poultry comprising, in a physiological medium, an inactivated or live attenuated *E. coli* strain expressing high level of α-Gal, in particular an efficient amount of *E. coli* strain selected in the group consisting of *E. coli* Nissle 1917 strain, *E. coli* O111 strain, *E. coli* O86:B7 strain, and mixture thereof.

Depending of the pathogenicity of the *E. coli* strain used, we may use killed or alive strain. Advantageously, we may live attenuated or inactivated (killed) strain.

The three principal vaccines types are: inactivated vaccines (whole cells killed bacteria and fractional inactivated vaccine), live attenuated vaccine and DNA-based vaccine.

In oral administration route, the vaccine powder could be spread on the animal feed using an adhesive agent like edible oils or gelatine, or the vaccine could be incorporated into the feed during the feed preparation process. For liquid vaccine, it is important to shake vigorously the content before administration, in order to avoid any separation of vaccine components that may occur during the storage period.

As an example, oral immunization using feed-based inactivated whole cell vaccine against aquaculture diseases was disclosed in Mohamad A. et al., MDPI, Vaccines 2021, 9, 368.

The efficient amounts of *E. coli* strains may be the same as the ones disclosed above for feed additive.

The man skilled in the art will develop oral vaccines according to his knowledge in oral immunization of such non-human animals, in particular fish and poultry.

The invention will further be illustrated by the non-limitative examples disclosed hereunder.

EXAMPLES

Example 1: Selection of *E. coli* Strains Having High Level of α-Gal

*E. coli* Strains

The *E. coli* Nissle 1917 strain is referred in scientific publications as a non-pathogenic *E. coli* strain (serotype O6:K5:H1) having accession number DSM 6601 that was deposited under the terms of the Budapest Treaty on Jul. 11, 1991 in the German Collection for Microorganisms, DSMZ-Deutsche Sammlung von Mikrooganismen and Zellkulturen GmbH, located at Mascheroder Weg 1 b, D-38124, Braunschweig, Germany (EP1636389). This strain is well characterized as its completed genome was sequenced (Reister et al., 2014).

The *E. coli* O86:B7 strain is an *E. coli* strain with serotype O86:K61(B7) available from the American Type Culture Collection (ATCC® 12701™; designation CDC6019-50; deposited name: *Escherichia coli* (Migula) Castellani and Chalmers).

The *E. coli* O111 strain is an *E. coli* strain with serotype O111:K58(B4):H—acquired from the American Type Culture Collection (ATCC® 33780™; designation Stoke W; deposited name: *Escherichia coli* (Migula) Castellani and Chalmers.

The *E. coli* O128 strain (Cigleris) is an *E. coli* strain with serotype O128:H2 having accession number DSM 8703 that was deposited under the terms of the Budapest Treaty before 12.1.1993 in the German Collection for Microorganisms, DSMZ-Deutsche Sammlung von Mikrooganismen and Zellkulturen GmbH, located at Mascheroder Weg 1b, D-38124, Braunschweig, Germany. Its name is *Escherichia coli* (Migula 1895) Castellani and Chalmers 1919. This strain is also referred in scientific publications Oerskov, I. (1977). Serology, chemistry, and genetics of O and K antigens of *Escherichia coli. Bacteriol. Rev.* 41: 667-710 and Beutin, L. (1990). Die Bedeutung and Erkennung von *Escherichia coli* als Krankheitserreger beim Menschen. *Bundesgesundheitsblatt* 9: 380-386. (https://www.dsmz.de/collection/cataologue/details/culture/DSM-8703).

The *E. coli* O113 strain is an *E. coli* strain with serotype O113:H21—acquired from the American Type Culture Collection (ATCC® BAA176™; designation: CDC 2001-3004; deposited name: *Escherichia coli* (Migula) Castellani and Chalmers.

The presence and level of α-Gal was detected in several *E. coli* strains by immunofluorescence and flow cytometry according to the following protocol:

The *E. coli* cells from each strain were washed in PBS and then fixed and permeabilized with the Intracell fixation and permeabilization kit (Immunostep, Salamanca, Spain) following manufacturer recommendations. Fixed cells were incubated for 1 h at room temperature (RT) with 3% Human Serum Albumin (HSA, Sigma-Aldrich, MO, USA) in PBS. The monoclonal mouse anti-α-Gal antibody (mAb) M86 (Enzo Life Sciences, Farmingdale, N.Y.) diluted 1:50 in 3% HSA/PBS was used as primary Ab (incubation for 14 h at 4° C.) and the FITC-conjugated goat anti-mouse IgM (Abcam, Cambridge, UK) diluted 1:200 in 3% HSA/PBS as a secondary Ab (incubation for 1 h at RT). Detection of α-Gal by flow cytometry was performed as previously described (Cabezas-Cruz et al., 2018). The samples were analyzed on a FACSCalibur flow cytometer equipped with CellQuest Pro software (BD Bio-Sciences, Madrid, Spain). The cell population was gated according to forward-scatter and side-scatter parameters. The human promyelocytic leukemia HL60 cells, that do not express α-Gal, were included as a negative control. The mean and median fluorescence intensity (MFI) of *E. coli* cells (BL21, EC1917, O111, O86:B7, 0128 and O113) was recorded and compared.

In a first experiment, the MFI values were measured for *E. coli* O86:B7, *E. coli* Nissle EC1917 and *E. coli* BL21:

*E. coli* O86:B7 (MFI=552)—High α-Gal

*E. coli* Nissle EC1917 (MFI=1092)—High α-Gal

*E. coli* BL21 (MFI=346)—Low α-Gal

In a second experiment, the MFI values were measured and the results are presented in the following table 2:

| *E coli* strains as disclosed above | FITC-A mean | Positive |
|---|---|---|
| *E. coli* Nissle | 1536 | YES |
| *E. coli* Nissle only secondary | 143 | |
| *E. coli* O111 | 1505 | YES |
| *E. coli* O111 only secondary | 128 | |
| *E. coli* 0128 | 139 | NO |
| *E. coli* 0128 only secondary | 121 | |
| *E. coli* O113 | 131 | NO |
| *E. coli* O113 only secondary | 192 | |
| *E. coli* O86:B7 | 634 | Positive control |
| *E. coli* O86:B7 only secondary | 123 | |
| *E. coli* ClearColi ® BL21(DE3) | 218 | Negative control |
| *E. coli* ClearColi ® BL21(DE3) only secondary | 200 | |
| *E. coli* BL21 | 128 | Negative control |
| *E. coli* BL21 only secondary | 124 | |

The strain *E. coli* ClearColi® BL21(DE3) Electrocompetent Cells (https://www.lucigen.com/ClearColi-BL21-DE3-Electrocompetent-Cells/). ClearColi is a genetically modified *E. coli* that lacks LPS. As LPS is where alpha-gal is mostly present on the cells glycans, ClearColi is an ideal negative control.

These data confirmed the results of the first experiment: *E. coli* Nissle and *E. coli* O86 are positive for alpha-gal (i.e., MFI higher than 500) and a new positive strain, *E. coli* O111, also have MFI above 500.

The other strains *E. coli* O128 and *E. coli* O113 are negative (i.e., MFI lower than 300). All the negative ones had MFI at the level of *E. coli* ClearColi® BL21(DE3) (this strain does not have LPS, so no alpha-gal because this glycan is in the LPS) and *E. coli* BL21 (our negative control).

For each strain, we included a negative control (only secondary antibody) that confirms that the fluorescence is not due to unspecific binding of the secondary antibody.

All these results confirmed that the 'selection criteria' (i.e., MFI above 500 for positive strains and MFI below 300 for negative strains) for the presence of alpha-gal is a good criteria and that the presence of alpha-gal in *E. coli* strain is a special trait that is not present in all the strains.

So an *E. coli* strain with 'high α-Gal content' or 'expressing high level of α-Gal' according to the present invention is a strain with MFI superior or equal to 500, preferably superior or equal to 530, more preferably superior or equal to 550.

The *E. coli* strain is advantageously selected in the group consisting of *E. coli* Nissle 1917*, E. coli* O111, *E. coli* O86:B7 and mixture thereof.

The following non-limitative examples demonstrated the protective effect of *E. coli* Nissle 1917 and *E. coli* O86:B7 against diseases in fishes and poultry. Similar results are expected with *E. coli* O111 strain that also has high level of α-Gal.

Example 2: Probiotic Effects of E Coil 1917 Strain on Fish 2.1 Materials & Methods Animal procedures were performed in accordance with Czech legislation (section 29 of Act no. 246/1992 Coll., on Protection of animals against cruelty, as amended by Act no. 77/2004 Coll.) and animal handling complied with the relevant European guidelines on animal welfare (Directive 2010/63/EU on the protection of animals used for scientific purposes) and the recommendations of the Federation of Laboratory Animal Science Associations.

Origin of Fish and Parasite

The immunization experiment was performed using specific pathogen-free (SPF) common carp (*Cyprinus carpio*), originating from fertilized eggs which were peroxide-treated (700 mg/L for 15 min), rinsed in dechlorinated tap water and incubated until hatching occurred. Carp were reared in a recirculation system (charcoal filtered tap water, UV filtration, ozone) at constant water temperature around 21° C., at the Animal Facility of the Institute of Parasitology (Biology Centre of the Czech Academy of Sciences). Feed was provided at a daily rate of at least 2% of biomass. Water quality was controlled weekly and ammonia levels kept <0.02 mg/L. Larvae were tested 1 week and 1.5 months after hatching for *S. molnari* infection-free status by specific PCR (Eszterbauer et al. 2013).

The *S. molnari* lab strain used for the experiment originates from a commercial carp culture pond in Vodňany, Czech Republic, which has been cycled in SPF fish for 3+ years, by fish-to-fish transmission via intraperitoneal (IP) injection of proliferative blood stages. Blood stages were harvested by bleeding fish from the caudal vein, using a heparinized syringe. Separation of the parasite from host cells was performed using an adapted DEAE cellulose column protocol (Lanham et al. 1970).

Preparation of Bacteria

Three different *E. coli* strains, Nissle 1917 (expressing high level of α-Gal), O86:B7 (expressing high level of α-Gal) and BL21 (expressing residual level of α-Gal), were grown on 50 ml of Luria Broth (LB, sigma), and incubated at 37° C. with vigorous shaking overnight. The bacterial cells were then washed 3 times with sterile PBS and a dilution of $2.5\times10^6$ colony-forming unit (CFU) per μl of PBS was prepared.

*E. coli* Nissle 1917 strain has accession number DSM 6601 that was deposited under the terms of the Budapest Treaty on Jul. 11, 1991 in the German Collection for Microorganisms, DSMZ-Deutsche Sammlung von Mikroorganismen and Zellkulturen GmbH, located at Mascheroder Weg 1 b, D-38124, Braunschweig, Germany.

*E. coli* BL21 strain is an *E. coli* BL21 (DE3) from Invitrogen (Carlsbad, Calif., USA)

*E. coli* O86:B7 strain is an *E. coli* strain with serotype O86:K61(B7) acquired from the American Type Culture Collection (ATCC® 12701™; designation CDC6019-50; deposited name: *Escherichia coli* (Migula) Castellani and Chalmers.

Oral Administration of Bacteria and Infection

Forty SPF carp of similar body size and averaging 13 g of body weight were randomly distributed between 4 aquaria off 40 L volume, with 10 fish in each group/aquarium. Water changes (75%) were performed 3 times a week, during the whole experiment. After a two weeks period of acclimatization, fish received 2 oral gavages (day 1 and day 21) of 200 μl either of PBS (control group), or of *E. coli* in PBS (3 different strains: BL21, O86:B7 or EC1917; $5\times10^8$ CFU each). *S. molnari* blood stages from a single donor fish were quantified in a Bürker chamber and 100 000 blood stages per fish were IP injected into the gavaged receptor fish, on day 30 (9 days after the second immunization). On day 57 (28 days post infection (dpi)), six fish of each group were bled and on day 68 (39 dpi) 8 fish were sampled, and the experiment was terminated.

Sampling Dates and Analyses

Based on the known infection profile and course of *S. molnari* in common carp (Korytář et al. 2019), samples for parasite quantification by qPCR were taken from the blood (28 dpi and 39 dpi), gill (39 dpi) and liver (39 dpi) and were analyzed as previously described (Korytář et al. 2019). Additionally, on both dates, basic host blood parameters were determined (hematocrit, leukocrit and number of erythrocytes and white blood cells). For hematocrit and leukocrit, heparinized capillaries were used and full blood was spun at 4 000 g for 5 min, before the amount of compacted erythrocytes and leukocytes relative to plasma were determined with a ruler. The number of erythrocytes, leukocytes and B lymphocytes was estimated by flow cytometry, using protocols for full blood analysis described previously (Korytář et al. 2013; 2019). Briefly, 2 μL of full blood were washed with cold RPMI and stained for 20 min with a monoclonal antibody recognizing the heavy chain of carp IgM (1 μg/ml) (Aquatic Diagnostics Ltd, Stirling, UK.), followed by staining with goat-anti-mouse IgG Alexa Fluor 488 (2 μg/ml; Thermo Fisher Scientific, Pardubice, Czech Republic). The samples were washed twice and resuspended in 200 μl of RPMI. Each sample was acquired for 20 seconds on BD FACSCanto II (BD Biosciences) with a flow rate of 60 μL $min^{-1}$. Erythrocytes were identified based on the forward scatter-width (FSC-W)/side scatter-area (SSC-A) profile as described earlier (Korytář et al. 2013), the proportion and total number of IgM+ B cells was determined by the Alexa Fluor 488 label. Individual weights of all fish were obtained at the end of the experiment (39 dpi).

Indirect ELISA

To evaluate levels of specific antibodies (Abs) in fish sera, 96-well ELISA plates (Nunc-Immuno™ Plate, Denmark) were coated overnight at 4° C. with 100 μl/well of either Galα1-3Gal linked to human serum albumin (HSA) (0.5 μg/ml; Dextra Laboratories, UK). The antigens were diluted in carbonate/bicarbonate buffer (0.05 M, pH 9.6). Optimal antigen concentration and dilutions of sera and conjugate were defined using titration assay. The wells were washed three times with 150 μl of PBS containing 0.05% Tween 20 (PBS-T) and then blocked with 1% HSA (Sigma-Aldrich, USA) in PBS-T for 1 h at 37° C. After five washes, serum samples, diluted in 0.5% HSA/PBS-T (1:800 for IgG; 1:400 for IgM and 1:10 for IgE), were added to the respective wells and incubated for 1 h at 37° C. The plates were washed five times and Abs (mouse anti-fish IgM; Bio-Rad, Germany) were added at 1:10,000 dilution in 0.5% HSA/PBS-T and incubated for 1 h at 37° C. The plates were washed five times and HRP-conjugated Abs (anti-mouse IgG; Bio-Rad, Germany) were added at 1:10,000 dilution in 0.5% HSA/PBS-T and incubated for 1 h at 37° C. Finally, the plates were washed five times and the reaction was developed by adding 100 μl ready-to-use TMB solution (Thermo Fisher Scientific, USA) at room temperature (RT) for 20 mins in the dark, and then stopped with 50 μl of 0.5 M $H_2SO_4$. Optical densities (OD) were measured at 450 nm using an ELISA plate reader (Filter-Max F5, Molecular Devices, USA). All samples were tested in triplicate and the average value of four blanks (no serum) was subtracted from the reads. The cut-off was determined as two times mean OD value of the blank controls. A monoclonal mouse anti-α-Gal antibody (mAb) M86 (Enzo Life Science Inc, USA), at dilution 1:100, was used as a positive control and HRP-goat anti-mouse IgM (diluted 1:4,000; Bio-Rad, Germany) as a secondary Ab.

2.2: Oral Administration of EC1917 Decreases the Severity of Sphaerosporosis in Fish Skin and gill sphaerosporosis in common carp is produced by *Sphaerospora molnari*, a myxozoan that produces α-Gal. *S. molnari* proliferation in the blood causes a massive inflammatory response in infected carp and spore-formation in the gills impedes respiration and osmoregulation, leading to high mortalities in pond aquaculture, especially in the summer months. In the laboratory model, parasite blood stages from donor fish were intraperitoneally injected into specific pathogen-free receptor fish (100 000 blood stages per fish), which had received 2 oral gavages (day 1 and day 21) either of PBS (control group), or *Escherichia coli* BL21, O86:B7 and EC1917 ($5\times10^8$ bacteria in 200 μl of PBS per fish per doses). Parasite proliferation rates in the receptor fish and basic host blood parameters were determined (hematocrit, leukocrit and number of erythrocytes as estimated by cytometry), 28 and 39 days after experimental infection with *S. molnari.*

Figure 1:
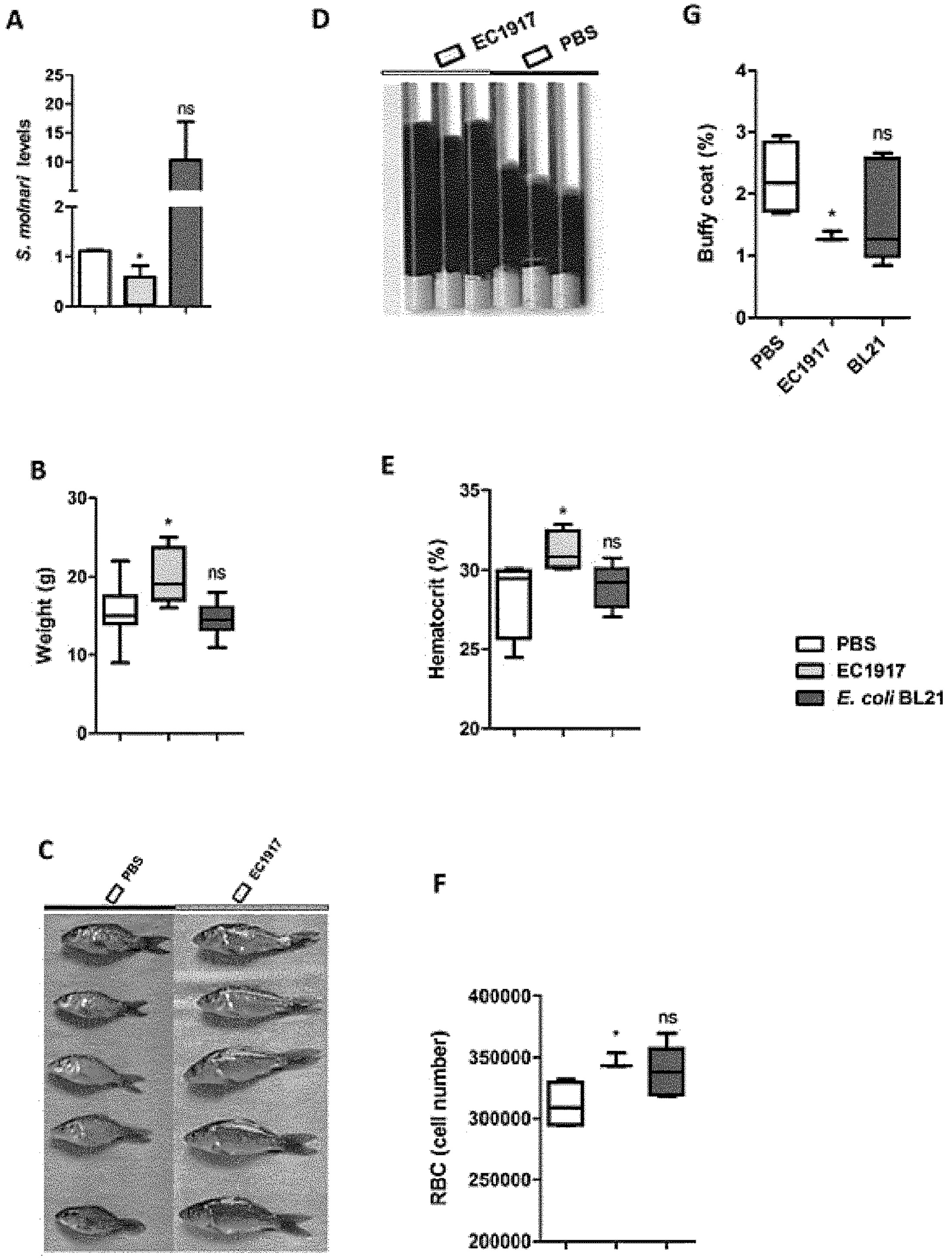
FIG. 1: Oral administration of EC1917 protects common carps against sphaerosporosis and promotes fish immunity and growth. The levels of *S. molnari* were measured in gills by real time PCR as previously reported (Parasit Vectors 2019; 12(2):208). 18S rRNA levels relative to infected PBS-treated fish (with EC1917 or BL21) were calculated using the $2^{-\Delta\Delta Ct}$ ratio method (Nucleic Acids Res. 2001; 29(9):e45) with *C. carpio* β-actin as the endogenous control gene (Parasit Vectors 2019; 12(2):208) (A). Fish weights were compared between groups (8) as well as the size of fish treated with EC1917 and with PBS (C). Hematocrit of blood collected from fish treated with EC1917 and PBS is presented (D) as well as the comparison of hematocrit values between groups (E). Capillary collected blood was also used to determine and compare the leukocrit (buffy coat) between groups (F). The boxes represent average and 10-90% percentiles. Results were compared by Student's t-test with unequal variance (*p<0.05; n=5/group, one biological replicate).

The parasite load was measured by real time PCR in blood, liver and gills. Results showed that oral administration with *E. coli* BL21 and *E. coli* O86:B7 did not have a significant effect on parasite load and fish physiology. However, fish treated with EC1917 have a significant reduction in the levels of *S. molnari* in gills (FIG. 1A) but not in blood and liver. In addition, despite being infected, the weight of the fish treated with EC1917 was significantly higher than that of the control group and the other two *E. coli* strains (FIG. 1B). A visual inspection confirms that EC1917-treated fish were bigger than the control (FIG. 1C).

These results demonstrate that the EC1917, in comparison to other strains, is able to reduce the level of *S. molnari* in gills and even promotes the growth of fish despite being infected. *Sphaerospora molnari* consumes erythrocytes and therefore produces anemia in infected fish. EC1917-treated fish had higher hematocrit (FIG. 1D, E) and red blood cells count (FIG. 1F) than the fish in the PBS group and the other two *E. coli* strains. The buffy coat that contains white cells and platelets was smaller in EC1917-treated fish compared to the other groups (FIG. 1G), indicating reduced inflammation, when compared with the control and the other groups. This suggests that oral administration of EC1917 decreases the inflammation induced by parasite infection.

With regard to the macroscopic pathology observed on day 39 post infection with *S. molnari*, it was noticeable that none of the EC1917 treated fish showed any pathological changes, while the control fish and several fish from other bacterial treatments showed enlarged kidneys and spleens.

All these data demonstrate that EC 1917 is efficient, in comparison to other strains, to provide protection against *S. molnari* in fish, decreases the inflammation induced by parasite infection and even promotes fish's growth, that is of interest in farmed fish.

Figure 2:
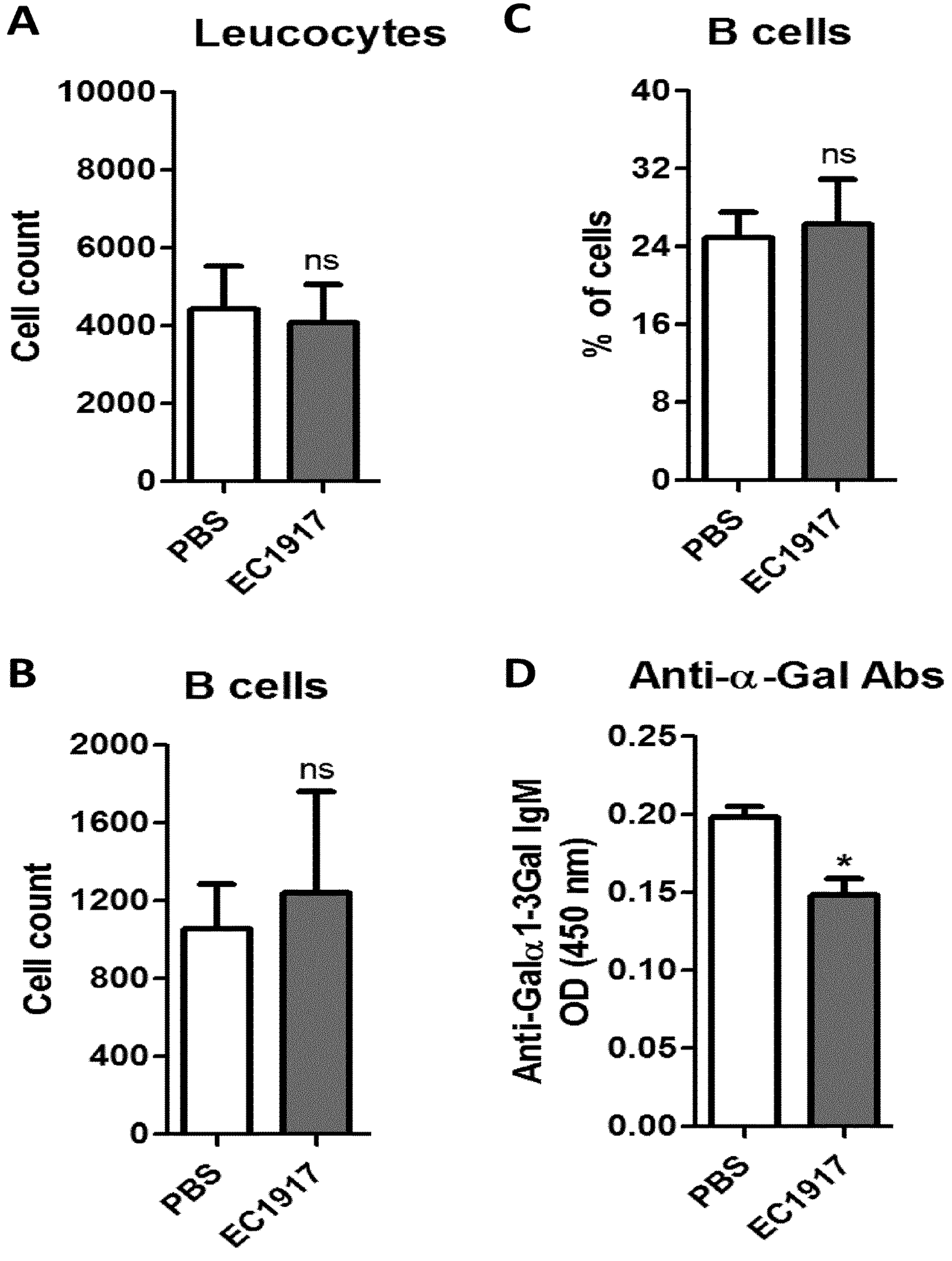
FIG. 2. Oral administration of EC1917 decreases the level of α-Gal Abs in sera of *S. molnari*-infected fish. Oral administration of EC1917 does not affect the number of leucocytes (A), B cells (8) and the percentage of B cells (C)

2.3: Oral Administration of *E. coli* 1917 Decreases the Levels of Anti-α-Gal Antibodies in Response to *S. Molnari* Infection Thirty-nine days after experimental infection with *S. molnari*, the animals were sacrificed and, to elucidate the development of adaptive immunity, Leucocytes and B cell kinetics and the secretion of specific anti-α-Gal IgM antibodies (Abs) in the blood were analyzed. No significant changes in the count of leucocytes (FIG. 2A), B cells (FIG. 2B) and the percentage % of B cells (FIG. 2C) were observed in the fish that were gavaged with the three strains of *E. coli*. However, oral administration of *E. coli* produced a significant decreased in the levels of anti-α-Gal Abs (FIG. 2D).

This result demonstrates that *E. coli* 1917 modulates the α-Gal immunity system.

Example 3: Probiotic Effects of *E. coli* O86:67 on Poultry 3.1 Materials and Methods All procedures in this work were performed according to the principles established by the French and International Guiding Principles for Biomedical Research Involving Animals (2012). The regional ethics committee for animal experimentation at the Veterinary College of Alfort approved this research (Anses/EnvA/UPEC, approval No. 10/03/15-11).

Animals and Housing Conditions

One-day old female turkeys (Hybrid Diamond White Medium strain, Grimaud Freres Selection, La Corbiére, France) and chickens (Lohmann Brown strain, Lohmann France, Le Grand Moulin, France) were purchased with an average weight of 40-50 g (chicken) and 65-70 g (turkeys). The animals were housed in cages (Ducatillon, Cysoing, France) under Specific-pathogen-free (SPF) conditions in the biosafety level 3 sector of the animal facility of the Veterinary College of Alfort (CRBM-EnvA). Fresh commercial turkey (Axereal, Olivet, France) and chicken starter food (Versele-Laga, Deinze, Belgium) and fresh water were provided ad libitum. Photoperiod cycles (14 h per day) and room temperature (25° C.) were controlled. Additional heat was provided by two infrared lamps located close to the animals.

*Aspergillus fumigatus* Strain and Inoculum Preparation

The highly germinative *A. fumigatus* CBS 144.89 (CEA10) clinical strain was used for all experiments (Kowalski et al., 2016). All mycological cultures were performed on Sabouraud dextrose agar (SDA) supplemented with chloramphenicol (5 mg/L) and incubated at 37° C. for 10 days. Sub-cultured were performed twice a week. To prepare the inoculum, *A. fumigatus* colonies were grown for 2-3 days at 37° C. Conidia were subsequently harvested by resuspension on PBST, filtered in a 70 μm diameter nylon cell strainer (ClearLine Dominique Dutscher, Brumath, France), washed by centrifugation at 3500 g for 10 min, resuspended in PBST and then counted using a Malassez counting chamber. The inoculum of *A. fumigatus* contained $4\times10^7$ conidia resuspended in 200 μl of PBST.

Detection of α-Gal Glycan in Fungi

The presence of α-Gal was detected in *A. fumigatus* by immunofluorescence, flow cytometry and inhibition ELISA.

For immunofluorescence, *A. fumigatus* conidia were prepared as described above and hyphae were separated from SDA media using PBS by gently scrapping. Conidia and hyphae were washed in PBS and then fixed and permeabilized with the Intracell fixation and permeabilization kit (Immunostep, Salamanca, Spain) following manufacturer recommendations. Fixed conidia and hyphae were incubated for 1 h at room temperature (RT) with 3% Human Serum Albumin (HSA, Sigma-Aldrich, MO, USA) in PBS. The monoclonal mouse anti-α-Gal antibody (mAb) M86 (Enzo Life Sciences, Farmingdale, N.Y.) diluted 1:50 in 3% HSA/PBS was used as primary Ab (incubation for 14 h at 4° C.) and the FITC-conjugated goat anti-mouse IgM (Abcam, Cambridge, UK) diluted 1:200 in 3% HSA/PBS as a secondary Ab (incubation for 1 h at RT). Hyphal mitochondria were stained with Mitotracker Red (Thermo Scientific, Waltham, Mass., USA). Aliquots of fixed and stained conidia were used for immunofluorescence assays, mounted in glass slides using ProLong Antifade with DAPI reagent (Molecular Probes, Eugene, Oreg., USA) and examined using a Zeiss LSM 800 laser scanning confocal microscope (Carl Zeiss, Oberkochen, Germany) with oil immersion objectives.

Detection of α-Gal by flow cytometry was performed as previously described (Cabezas-Cruz et al., 2018). Briefly, samples were analyzed on a FACSCalibur flow cytometer equipped with CellQuest Pro software (BD Bio-Sciences, Madrid, Spain). The cell population was gated according to forward-scatter and side-scatter parameters. The human promyelocytic leukemia HL60 cells, that do not express α-Gal, were included as a negative control. The mean and median fluorescence intensity of HL60 and conidia was recorded and compared.

Fungal proteins were extracted with six steel balls using the homogenizer Precellys®24 Dual (Bertin, France) at 6000 rpm for 30 s followed by cool down in ice, 3 times in PBS-1% triton and quantified by Bicinchoninic Acid (BCA) Protein Assay Kit (ThermoFisher, Waltham, Mass., USA) with BSA as standard.

For inhibition ELISA, the inhibition of M86 binding to Galα1-3Gal linked to HSA (Galα1-3Gal-HSA, Dextra Laboratories, Reading, UK) was calculated after pre-incubation of M86 with fungal proteins. Briefly, 96-well ELISA plates (Nunc-Immuno™ Plate, Roskilde, Denmark) were coated overnight at 4° C. with Galα1-3Gal-HSA (50 ng/well) diluted in carbonate/bicarbonate buffer (0.05 M, pH 9.6). The wells were washed three times with 150 μl of PBST and then blocked with 0.5% HSA/PBST for 1 h at RT. The mAb M86 diluted 1:200 was pre-incubated overnight at 4° C. and constant shaking of 300 rpm with two concentrations of fungal proteins (i.e. 0.5 μg/ml and 1.5 μg/ml). Pre-incubation with α-Gal-BSA and protein extract of ggta1 knockout (KO) *Sus scrofa* (pig) were used as positive and negative controls, respectively. The protein-mAb M86 complexes were removed by centrifugation at 16.000 g for 30 min at 4° C. The supernatant (containing free mAb M86) was then collected and added to the Galα1-3Gal-HSA-coated wells for 1 h at 37° C. The plates were washed three times and horseradish-peroxidase (HRP)-conjugated goat anti-mouse IgM Ab diluted 1:2000 was used as secondary Ab and incubated at RT for 1 h. The plates were washed three times and the reaction was developed by adding 100 μl ready-to-use tetramethylbenzidine-hydrogen peroxide (TMB) solution (Promega, Madison, USA) at RT for 20 min in the dark, and then stopped with 50 μl of 0.5 M H2SO4. The optical densities (OD) were measured at 450 nm using an ELISA plate reader (Filter-Max F5, Molecular Devices, San Jose, Calif., USA). All samples were tested in triplicate and the average value of three blanks (no Abs) was subtracted from the reads. The cut-off was determined as two times of a mean OD value of the blank controls. The percentage of M86 binding inhibition was calculated using the average OD of each sample as 100-(100×OD$_{(M86\ after\ pre\text{-}incubation\ with\ fungal\ proteins\ or\ \alpha\text{-}Gal\text{-}BSA\ or\ protein\ extract\ 204\ of\ ggta1\ KO\ pigs)}$/OD$_{(M86\ without\ pre\text{-}incubation)}$).

Bacteria Culture and Oral Administration of Bacteria

The bacteria *E. coli* O86:B7 (ATCC 12701) expresses high levels of α-Gal on its surface, which is not the case for *E. coli* BL21 (DE3, Invitrogen, Carlsbad, Calif., USA). The *E. coli* strains were grown on 50 ml of Luria Broth (Sigma-Aldrich, MO, USA), incubated at 37° C. with vigorous shaking overnight, washed twice with PBS, centrifuged at 4000 g for 5 min at 4° C. and re-suspended at a concentration of ~1×10$^{10}$ colony-forming units (CFU)/ml of PBS. For oral administration of bacteria, 7-days old turkeys (n=20) received *E. coli* strain O86:B7 (n=10) or *E. coli* strain BL21 (n=10) (~1×10$^{9}$ CFU in 100 μl of PBS) via oral gavage at days 0, 1, 3, 7, 8, 9, 14, 15 and 16.

Immunization

For immunization, 7-days old turkeys (n=20) and chickens (n=10) were immunized subcutaneously with synthetic Galα1-3Gal conjugated to BSA (α-Gal-BSA, Dextra Laboratories, Reading, UK) (75 218 μg/bird) in 200 μl of the water-in-oil emulsion of 70% Montanide ISA adjuvant (SEPPIC, France), with a boost 2 weeks later (day 14). Control animals received a mock vaccine (PBS and adjuvant).

Intratracheal Challenge with *A. fumigatus*

The intratracheal challenge was performed on day 27. Before fungal inoculation, birds were anesthetized by inhalation of 5% isoflurane (Aerrane, Baxter, Maurepas, France) in oxygen until unconsciousness. Inoculation of *A. fumigatus* (200 μl PBST containing an infectious dose of 4×10$^{7}$ conidia) was performed using a 1 ml syringe (Medallion, Merit Medical, The Netherlands) fitted with a stainless steel 19-gauge aerosolizer (Microsprayer 1A-1B, Penn Century, PA, USA). The gauge was inserted through the oropharynx into the trachea under visual control. After challenge, birds were monitored twice a day on a daily basis. Respiratory signs of avian aspergillosis (i.e. open-mouthed breathing, gasping and hyperpnea) were recorded. Animals were sacrificed 4 days after challenge.

Euthanasia, Lung Lesions Score and Sample Collection

On day 31, four days after the infectious challenge, birds were anesthetized and euthanized by occipital sinus injection of 182.20 mg/kg of sodium pentobarbital (Dolethal, Vetoquinol, Lure, France). The respiratory tract was removed aseptically under a laminar flow cabinet and the presence and size of lesions in the right and left lungs were registered. Observed lung lesions varied among congestive, haemorrhagic or consolidated/indurated lesions. They were classified according to the following score: no lesions (minimum score, 0); small lesions between 1 cm$^2$ and 2 cm$^2$ (score 1); moderate-size lesions between 3 cm$^2$ and 4 cm$^2$ (score 2) and extensive lesions with more than 4 cm$^2$ and covering almost all the area of the lungs (maximum score, 3). The statistical differences between groups were evaluated using one-way ANOVA with Dunnett's multiple comparison test applied for individual comparisons (for the groups treated with *E. coli* O86:B7, *E. coli* BL21 and PBS) and the unpaired non-parametric Mann Whitney's test (for the groups immunized with α-Gal-BSA and the mock vaccine) in the GraphPad 5 Prism program (GraphPad Software Inc., San Diego, Calif., USA). Differences were considered significant when $p<0.05$.

Blood samples were collected on days 0, 7, 14 and 31 on sterile tubes without anticoagulant. For serum separation, the blood samples were incubated for 20-30 min at RT, allowing for clotting, and then centrifuged at 1.500 g for 20 min at RT. After necropsy, samples from the right and left lungs were aseptically collected and conserved according to the analysis to be performed: samples for DNA (for *A.*

*fumigatus* 28S quantification by quantitative PCR (qPCR)), RNA (for cytokines quantification by qPCR) and protein (for anti-α-Gal IgA quantification) extraction were placed immediately in liquid nitrogen; samples for histopathology were immediately fixed in 10% Neutral Buffered Formalin (NBF) and the samples for CFU assay were conserved in PBST on ice until processing. Ceca samples were also collected (for RNA extraction and cytokines quantification by qPCR) and placed immediately in liquid nitrogen.

Indirect ELISA for Anti-α-Gal IgY and IgA Levels Determination

To evaluate levels of specific Abs against Galα1-3Gal and Galα1-3Galβ1-4GlcNAc in turkey and chicken sera, 96-well ELISA plates (Thermo Scientific, Waltham, Mass., USA) were coated with 100 μl/well of either Galα1-3Gal-HSA and Galα1-3Galβ1-4GlcNAc linked to HSA (0.5 μg/ml, Dextra Laboratories, Reading, UK) and incubated overnight at 4° C. The antigens were diluted in carbonate/bicarbonate buffer (0.05 M, pH 9.6) and incubated overnight at 4° C. Optimal antigen concentration and dilutions of sera and conjugate were defined using a titration assay. Wells were washed three times with 150 μl of PBST and then blocked by adding 100 μl of 1% HSA/PBST for 1 h at RT. After three washes, serum samples, diluted in 0.5% HSA/PBST (1:500), were added to the wells and incubated for 1 h at 37° C. The plates were washed three times and HRP-conjugated Abs (goat anti-turkey IgY (Mybiosource, California, USA) goat anti-chicken IgY (Sigma-Aldrich, MO, 267 USA) or goat anti-chicken IgA (CliniScience, Nanterre, France) were added at 1:2000 dilution in 0.5% HSA/PBST (100 μl/well) and incubated for 1 h at RT. The plates were washed three times and the reaction was developed by adding 100 μl ready-to-use TMB solution (Promega, Madison, USA) at RT for 20 min in the dark, and then stopped with 50 μl of 0.5 M H2SO4. The OD were measured at 450 nm using an ELISA plate reader (Filter-Max F5, Molecular Devices, San Jose, Calif., USA). All samples were tested in triplicate and the average value of three blanks (no Abs) was subtracted from the reads. The cut-off was determined as two times a mean OD value of the blank controls.

Determination of anti-α-Gal IgA levels in the lungs was performed as above, but using total lung proteins (600 ng), extracted by the TRI Reagent kit (Thermo Scientific, Waltham, USA) following manufacturer recommendations. The statistical differences between groups were evaluated using one-way ANOVA with Dunnett's multiple comparison test applied for individual comparisons in the GraphPad 5 Prism program (GraphPad Software Inc., San Diego, Calif., USA). Differences were considered significant when $p<0.05$.

Enzymatic Removal of α-Gal to Test the Specificity of Turkey Anti-α-Gal Abs

To assess the specificity of anti-α-Gal Abs in turkeys, the Galα1-3Gal-HSA antigen (Dextra Laboratories, Reading, UK) was immobilized on an ELISA plate (50 ng/well), and treated or not with α-galactosidase from green coffee beans (Sigma-Aldrich, MO, USA) following the procedure described in Iniguez et al. 2017. Before the treatment, the enzyme was centrifuged at 10.000 g for 10 min at 4° C., to remove the ammonium sulfate. The supernatant was discarded and 100 mM potassium phosphate buffer (pH 6.5) was added to the pellet so the final concentration of the enzyme solution was 50 mU/100 μl. The plate was then incubated at 37° C. for 24 h in a humidified plastic chamber to avoid evaporation. After the incubation, wells were washed five times with 150 μl of PBST and the indirect ELISA was performed as described above. Sera samples from the turkeys treated with *E. coli* O86:B7 (n=5), *E. coli* BL21 (n=5) and PBS (n=5) were randomly selected and used in the specificity assay. The statistical differences of sera reactivity against treated and non-treated antigen were evaluated using the Wilcoxon signed rank test in the GraphPad 5 Prism program (GraphPad Software Inc., San Diego, Calif., USA). Differences were considered significant when $p<0.05$.

Histopathology and Histopathological Scores

Lung samples collected for histopathology were immediately fixed in 10% NBF for 48 h, then dehydrated in successive baths of ethanol (from 70 to 100%) and embedded in paraffin blocks using Fully Automated Innovative Tissue Processor LOGOS One (Milestone, Sorisole, Italy). Thick sections of 4 μm were cut out of the paraffin specimens and placed in slides. The slides were automatically stained with hematoxylin-eosin-saffron (HES) using Leica ST5010-CV5030 Integrated Workstation Leica, Nanterre, Germany). Periodic Acid-Schiff (PAS) staining was performed using the PAS kit (Sigma-Aldrich, MO, USA) following to the manufacturer instructions. A blind reading of five fields (100×) per slide of the right and left lungs of each turkey was conducted to visualize microscopic lesions associated with inflammation and granulomas (using slides stained with HES) and the presence of *Aspergillus*-like hyphae (using slides stained with PAS). Microscopic observations in each field were recorded and scored as follows for HES: absence of leukocyte infiltrate and peribronchial regions visible (minimum score, 0); leukocyte infiltrate surrounding peribronchial regions without lumen stenosis (score 1); intense leukocyte infiltrate and lumen of peribronchial regions is not visible (score 2); and presence of granulomas (maximum score, 3).

Fungal presence by PAS was scored as follows: absence of fungal elements (minimum score, 0); presence of isolated germ tube/hyphae (score 1), presence of several branching hyphae (mycelium) inside granulomas between 20 and 25 $\mu m^2$ (score 2) and presence of mycelium inside granulomas larger than 25 $\mu m^2$ (maximum score, 3). The scores of the five-field readings per slide and per staining were used to calculate the HES and PAS scores per lung and per animal. The statistical differences between groups were evaluated using one-way ANOVA with Dunnett's multiple comparison test applied for individual comparisons (for the groups treated with *E. coli* O86:B7, *E. coli* BL21 and PBS) and the unpaired non-parametric Mann Whitney's test (for the groups immunized with α-Gal-BSA and the mock vaccine) in the GraphPad 5 Prism program (GraphPad Software Inc., San Diego, Calif., USA). Differences were considered significant when $p<0.05$.

Quantification of *A. fumigatus* by CFU and qPCR Assays

For CFU counting, 100 mg of right lungs were individually ground in 5 ml of PBST using the Bio-Gen PRO200 Tissue Homogenizer (PRO Scientific, Oxford, Conn., USA). An aliquot of the lung homogenate (100 μl) was immediately spread on SDA plates and incubated at 37° C. for 24 to 48 h, after which *A. fumigatus* colonies counting was performed. For qPCR, genomic DNA was extracted from 25 mg of the right lungs. The lung samples were individually crushed in 180 μl of Lysis Buffer (QIAamp DNA Mini Kit, Qiagen, Courtaboeuf, France) with glass beads using the Tissue Homogenizer 125 Precellys 24 (Bertin Technologies, Montigny-le-Bretonneux, France) at 6000 rpm for 30 s. The homogenization procedure was repeated three times with a 30 s cooling period in ice in between cycles. DNA extraction was completed using the QIAamp DNA Mini Kit (Qiagen, Courtaboeuf, France) according to the manufacturer instructions.

qPCR was performed with 100 ng of genomic DNA targeting *A. fumigatus* 28S gene with SYBR Green LightCycler 480 Master mix (Roche, Meylan, France). All assays were run under the same conditions as follow: 50° C. for 2 min, 95° C. for 10 min, and 45 cycles of 15 s at 95° C. and 1 min at 60° C. The CT values were recorded, and the relative levels of fungal DNA were normalized against turkey β actin (actb) and glyceraldehyde-3-phosphate dehydrogenase (gapdh) and chicken gapdh as host genes using the $2^{-\Delta\Delta Ct}$ ratio method. All primers are available in the following Table 3.

MyD88, IL6 and IL10 (Table 3 disclosed above). The LightCycler 480 System Thermocycler (Roche, Basilea, Suiza) was used. The qPCR assays were run under the following conditions: 50° C. for 2 min, 95° C. for 10 min, then 45 cycles of 15 s at 95° C. and 1 min at 60° C. The CT values were recorded and the $2^{-\Delta\Delta Ct}$ method was used to calculate the relative gene expression values with turkey actb and gapdh and chicken gapdh as the endogenous control genes. Statistical differences between groups for each gene were evaluated using one-way ANOVA with Dunnett's multiple comparison test applied for individual comparisons in the GraphPad 5 Prism program (GraphPad Software Inc., San Diego, Calif., USA). Differences were considered significant when p<0.05.

TABLE 3

| Gene | Target species | NCBI Target gene(s) | Forward primer | SEQ ID NO: | Reverse primer | SEQ ID NO: | Target length |
|---|---|---|---|---|---|---|---|
| GAPDH | Chicken<br>Turkey | NM_204305<br>NM_001303179 | CCACATGGCATCCAAGGAGT | 1 | CTCCAACAAAGGGTCCTGCT | 2 | 74 bp |
| β-actin | Chicken<br>Turkey | L08165.1<br>AY942620.1 | GAGAAATTGTGCGTGACATCA | 3 | CCTGAACCTCTCATTGCCA | 4 | 114 bp |
| IL-2 | Chicken | AF017645 | TTGGCTGTATTTCGGTAGCA | 5 | TCCTGGGTCTCAGTTGGTGT | 6 | 160 bp |
| IL-2 | Turkey | AJ007463 | GAGCATCGCTATCACCAGAA | 7 | GCAGAGTTTGCTGACTGCAC | 8 | 141 bp |
| IL-6 | Chicken<br>Turkey | AJ309540<br>XM_003207130 | AGGGCCGTTCGCTATTTGAA | 9 | ACGGAACAACACTGCCATCT | 10 | 112 bp |
| IL-10 | Turkey | NM_001303189 | GCTGCGCTTCTACACAGATG | 11 | TCCCGTTCTCATCCATCTTC | 12 | 203 bp |
| IL-4 | Turkey | NM_001303181.<br>1 | AGAGCTCATTGCCTCCACAC | 13 | ATTGCAAGGGACCTGCTCTC | 14 | 72 bp |
| MyD88 | Turkey | XM_019616228.<br>1 | TTACGAAGGAAGCAGCAGGAG | 15 | TGGCAAGACATCCCGATCAA | 16 | 208 bp |
| IFN-γ | Turkey | XM_003202048 | CTGAAGAACTGGACAGAGAG | 17 | CACCAGCTTCTGTAAGATGC | 18 | 264 bp |
| 28S | *A. fumigatus* | NG_055745.1 | CTCGGAATGTATCACCTCTCGG | 19 | TCCTCGGTCCAGGCAGG | 20 | 29 bp |

The statistical differences between groups were evaluated using one-way ANOVA with Dunnett's multiple comparison test applied for individual comparisons (for the groups treated with *E. coli* O86:B7, *E. coli* BL21 and PBS) and the unpaired non-parametric Mann Whitney's test (for the groups immunized with α-Gal-BSA and the mock vaccine) in the GraphPad 5 Prism program (GraphPad Software Inc., San Diego, Calif., USA). Differences were considered significant when p<0.05.

RNA Extraction and Quantification of Cytokines mRNA Levels by qPCR

Total RNA was extracted from 100 mg of right lung and ceca samples. Tissue samples were individually crushed in 1 ml of TRI Reagent (Thermo Scientific, Waltham, Mass., USA) with glass beads using the Tissue Homogenizer 125 Precellys 24 (Bertin Technologies, Montigny-le-Bretonneux, France) at 6000 rpm for 30 s. The homogenization procedure was repeated three times. Complementary DNAs (cDNA) were obtained by reverse transcription of total RNA (1 μg) using random primers and the SuperScript VILO cDNA Synthesis Kit (Thermo Scientific, Waltham, Mass., USA). Equal amounts of cDNA per sample (10 ng) were used in triplicate assays for qPCR amplification using the SYBR Green LightCycler 480 Master mix (Roche, Meylan, France) with 0.3 μM of each primer for the genes IL2, IFNγ, 3.2 *A. fumigatus* Contains the Carbohydrate α-Gal Immunofluorescence labeling using the anti-α-Gal mAb M86 confirmed the presence of α-Gal glycan on the surface and cytoplasm of *A. fumigatus* conidia as well as in the cytoplasm of its hyphae and forming granular structures on the surface of hyphal stretches (data not shown).

The binding of the mAb M86 to α-Gal epitopes in *A. fumigatus* was further confirmed by flow cytometry (FIG. 3A). The association of α-Gal to fungal proteins was assessed by an inhibition ELISA in which the reactivity of mAb M86 was measured following a pre-incubation with protein extracted from *Aspergillus fumigatus* (FIG. 3B).

3.3 Oral Administration of *E. coli* O86:B7 Reduces Clinical Signs of Aspergillosis and Development of Lung Granulomas in *A. fumigatus*-Infected Turkeys Daily clinical examination of challenged birds revealed that oral administration of highly α-Gal expressing *E. coli* O86:B7 protects the turkeys from developing respiratory clinical signs associated with avian aspergillosis such as open-mouthed breathing (OMB, FIG. 4A), gasping and hyperpnea. This was not the case for PBS-treated (FIG. 4A) nor *E. coli* BL21-treated (FIG. 4A) turkeys. Four-days post-infection, all birds were sacrificed. Assessment of macroscopic lung lesions (FIG. 4B) showed lungs of turkeys treated with PBS and *E. coli* BL21 with lesions suggesting granulomas that in some cases covered the whole organ (score 3, FIG. 4B). This resulted in lesional scores significantly higher than those of *E. coli* O86:B7-treated animals in which granulomas were scarce (FIG. 4C). Notably, only one turkey developed a small granuloma (score 1, FIG. 4B) in the right lung. Scoring of histopathological lung lesions considered the level of inflammation and granulomas assessed by HES staining (HES score, FIG. 4D) and the presence of hyphae assessed by PAS (PAS score, FIG. 4E). Animals treated with *E. coli* O86:B7 had significant lower inflammation (FIG. 4F) and hyphae (FIG. 4G) scores than those treated with PBS and *E. coli* BL21. Lung samples were homogenized and applied either on agar for CFU counting assay or used for 28S DNA quantification by qPCR. No significant differences in *A. fumigatus* CFU or 28S DNA was observed between groups (FIGS. 4H and 4I). However, some animals in the *E. coli* O86:B7-treated group had 2-fold increase in the 28S levels, possibly related with the presence of damaged fungal elements.

3.4 Oral Administration of *E. coli* O86:B7 Decreases Anti-α-Gal IgA Production in the Lungs of *A. fumigatus*-Infected Turkeys Natural Abs have affinity for different α-Gal-related antigens including Galα1-3Gal disaccharide and Galα1-3Galβ1-4GlcNAc trisaccharide. Sera levels of immunoglobulin Y (IgY) and IgA against Galα1-3Gal and Galα1-3Galβ1-4GlcNAc were measured by ELISA in sera from turkey that received PBS only. The levels of circulating IgY against Galα1-3Gal did not change over time (FIG. 5A), while the levels of anti-Galα1-3Galβ1-4GlcNAc IgY significantly increased at day 31 (FIG. 5B). Only residual levels of circulating IgA against Galα1-3Gal were detected, and the level of these Abs did not changed over time (FIG. 5C).

Turkeys that received *E. coli* O86:B7 or *E. coli* BL21 orally showed no change in the levels of circulating IgY against Galα1-3Gal and only those treated with *E. coli* O86:B7 showed higher levels of circulating IgY against Galα1-3Galβ1-4GlcNAc at day 7. The turkeys that received *E. coli* O86:B7 showed lower levels of circulating IgY against Galα1-3Gal at day 14 than turkeys that received PBS (FIG. 5D), an effect not observed in turkeys that received *E. coli* BL21. At day 31, anti-Galα1-3Gal IgY levels were higher in animals that received *E. coli* O86:B7 and *E. coli* BL21 compared with animals that received PBS. However, turkeys treated with *E. coli* O86:B7 showed lower levels of anti-Galα1-3Galβ1-4GlcNAc IgY at day 31 than animals that received *E. coli* BL21 or PBS (FIG. 5E).

The specificity of the reactivity of turkey sera to Galα1-3Gal was tested by enzymatic removal of terminal α-Gal residues from Galα1-3Gal-HSA. A significant decrease in the sera reactivity after the enzymatic removal of terminal α-Gal residues from Galα1-3Gal-HSA antigen was observed in turkeys from all groups (FIG. 6A).

Lung proteins obtained from lung samples at day 31 (four days after infection) allowed the detection of IgA against Galα1-3Gal and Galα1-3Galβ1-4GlcNAc by ELISA. Only residual levels of anti-Galα1-3Gal and anti-Galα1-3Galβ1-4GlcNAc IgA Abs were detected in the lungs of turkeys that received *E. coli* O86:B7 (FIG. 6B). This was not the case for *E. coli* BL21-treated or PBS-treated turkeys (FIG. 6B). Positive correlations between the levels of anti-Galα1-3Gal or anti-Galα1-3Galβ1-4GlcNAc IgA and the granulomas score in the lungs were found (FIG. 6C). There was no correlation between levels of anti-Galα1-3Gal and anti-Galα1-3Galβ1-4GlcNAc IgY and normalized *A. fumigatus* 28S gene levels (data not shown).

3.5 Immunization Against Galα1-3Gal Increases Fungal Development in the Lungs

Four days after infection, infected PBS-immunized turkeys developed significantly more lung granulomas and higher CFU when compared with chickens (FIG. 7).

Immunization of turkeys using synthetic Galα1-3Gal conjugated to BSA (α-Gal-BSA), elicited the production of circulating IgY with affinity for Galα1-3Gal (FIGS. 8A and 9A). This Ab production did not modify the granulomas score (FIG. 8B), the number of CFU (FIG. 8C), nor the HE and PAS scores (data not shown) compared with control group that received the mock vaccine. Furthermore, the normalized levels of *A. fumigatus* 28S were significantly higher in the lungs of turkeys immunized with α-Gal-BSA (FIG. 8D), compared with the control group. No significant changes were observed in IgY production against Galα1-3Galβ1-4GlcNAc (FIG. 9B), in the levels of serum anti-Galα1-3Gal IgA (FIG. 9C), in the lung levels of anti-Galα1-3Galβ1-4GlcNAc IgA (FIG. 9D) or of anti-Galα1-3Gal IgA Abs (FIG. 9E).

In chickens, α-Gal-BSA immunization also elicited a significant increase in circulating anti-Galα1-3Gal IgY Abs (FIG. 8E and FIG. 9F) and circulating anti-Galal-3Gal IgA Abs in immunized chicken remained similar to the control group (FIG. 9G). Of the five chickens immunized with α-Gal-BSA, four developed granulomas, two in the right and left lungs and two in the left lung only. In contrast, one animal of the control group developed granulomas in the right and left lungs. Despite a tendency to increase, no significant difference was observed in the granulomas score (FIG. 8F) nor in the CFU number (FIG. 8G) between the α-Gal-BSA-immunized group and the control group. Notably, as per turkeys (FIG. 8D), immunized chickens had a significant increase in the levels of *A. fumigatus* 28S in lungs (FIG. 8H).

3.6 Immunization Against Galα1-3Gal is Associated with Upregulation of Proinflammatory Cytokine Genes in *A. fumigatus*-Infected Turkeys and Chickens The inventors tested whether oral administration of *E. coli* O86:B7 has an effect on the expression of genes encoding for pro-inflammatory (i.e. IFNγ, IL6, IL2) and anti-inflammatory (i.e. IL10) cytokines, as well as on the expression of innate immune receptor genes (i.e MyD88) in the ceca and lungs of *A. fumigatus*-infected turkeys. MyD88 transcription was also assessed in turkeys treated with *E. coli* BL21 or immunized with α-Gal-BSA. The effect of α-Gal-BSA immunization on the expression of proinflammatory cytokines (i.e. IL6 and IL2) and of MyD88 adaptor in the lungs of *A. fumigatus*-infected chicken was also tested.

After cDNA normalization with the PBS control group, MyD88, IFNγ and IL6 expression was significantly upregulated in the ceca of α-Gal-BSA-immunized turkeys (FIG. 10A). α-Gal-BSA immunization also induced a significant upregulation of IL2 in turkey (FIG. 10B) and chicken lungs and IL6 only in chicken lungs (FIG. 10C). Oral administration of *E. coli* BL21 in turkeys was associated with upregulation of IL10, IFNγ and IL6 expression in ceca (FIG. 10A) and IL6 expression in lungs (FIG. 10B). Notably, except for IL2 for which a 27.8-fold increase was observed in ceca (FIG. 10A), oral administration of *E. coli* O86:B7 was not associated with significant changes in the mRNA levels of the tested genes (FIGS. 10A and B).

These data demonstrated that oral administration of *E. coli* O86:B7 protects non-mammalian vertebrates against a fungal pathogen expressing α-Gal on its surface. In this study, oral administration of *E. coli* O86:B7 protects turkeys from developing clinical and lesional aspergillosis. However, in contrast with the previous results by Yilmaz et al. (2014), the protective effect of *E. coli* 567 O86:B7 was not associated with an increase in the levels of anti-α-Gal Abs, but with a significant reduction in the levels of circulating IgY Abs with reactivity to Galα1-3Galβ1-4GlcNAc and IgA Abs with reactivity to Galα1-3Galβ1-4GlcNAc and Galα1-3Gal in the lungs of *A. fumigatus*-infected animals. It is noteworthy that Yilmaz et al. (2014) administered *E. coli* O86:B7 ($\sim 10^7$ CFU) 3 times at two weeks intervals, while 3 consecutive administrations of *E. coli* O86:B7 ($\sim 10^9$ CFU) repeated 3 times at 4 days intervals were used in the present study. These results suggest that the continuous administration of large doses of highly α-Gal expressing *E. coli* O86:B7 decreased or totally abrogated responsiveness to the α-Gal on the surface of *A. fumigatus*.

These data also demonstrated that oral administration of *E. coli* O86:B7 617 reduced the occurrence and severity of lung granulomas with no effect in the fungal burden, suggesting a mechanism where gut microbiota promotes disease tolerance in the lungs by preventing the upregulation of pro-inflammatory cytokines (i.e. IL2, IL6 and INFγ) and by decreasing the levels of anti-α-Gal Abs in response to *A. fumigatus* infection.

In the present study, the inventors showed that gut microbiota bacteria expressing high levels of α-Gal protects turkeys against aspergillosis. Continuous administration of *E. coli* O86:B7 abrogated the anti-α-Gal IgA response in the lungs of turkeys infected by *A. fumigatus*, a pathogen containing α-Gal on the surface. The absence of lung lesions in turkeys treated with *E. coli* O86:B7 and infected with *A. fumigatus* suggests that anti-α-Gal IgA are pro-inflammatory Abs that enhance the occurrence and development of lung lesions associated with acute aspergillosis.

The absence of lung lesions allowed the animals to tolerate the fungal infection with no clinical signs, which suggests the possibility of using gut microbiota bacteria expressing high levels of α-Gal to prevent acute aspergillosis in animals and humans.

The results of this study support the use of α-Gal expressing probiotic-based vaccines to modulate the α-Gal immunity, without the potential negative effects associated with other conventional vaccines using α-Gal as antigen.

REFERENCES

Beutin, L. (1990). Die Bedeutung and Erkennung von *Escherichia coli* als Krankheitserreger beim Menschen. *Bundesgesundheitsblatt* 9: 380-386

Cabezas-Cruz, A.; Espinosa, P. J.; Alberdi, P.; Šimo, L.; Valdés, J. J.; Mateos-Hernández, L.; Contreras, M.; Rayo, M. V.; de la Fuente J. Tick galactosyltransferases are involved in α-Gal synthesis and play a role during *Anaplasma phagocytophilum* infection and *Ixodes scapularis* tick vector development. *Sci Rep.* 2018, 8, 14224.

Eszterbauer E, Sipos D, Forró B, Ova P B, Holzer A S (2013) Molecular characterization of *Sphaerospora molnari* (Myzozoa), the agent of gill sphaerosporosis in common carp *Cyprinus carpio carpio. Dis Aquat Organ.* 104: 59-67.

Iniguez, E.; Schocker, N. S.; Subramaniam, K.; Portillo, S.; Montoya, A. L.; Al-Salem, W. S.; 804 Torres, C. L.; Rodriguez, F.; Moreira, O. C.; Acosta-Serrano, A.; et al. An α-Gal-containing 805 neoglycoprotein-based vaccine partially protects against murine cutaneous leishmaniasis caused by 806 *Leishmania major. PLoS Negl Trop Dis.* 2017, 11, e0006039.

Kowalski, C. H.; Beattie, S. R.; Fuller, K. K.; McGurk, E. A.; Tang Y. W.; Hohl, T. M.; Obar, J. J.; Cramer, R. A. Heterogeneity Among Isolates Reveals That Fitness in Low Oxygen Correlates With *Aspergillus fumigatus* virulence. *mBio.* 2016, 7, e01515-e01516. Korytář T, Dang Thi H, Takizawa F, Köllner B. (2013) A multicolour flow cytometry identifying defined leukocyte subsets of rainbow trout (*Oncorhynchus mykiss*). *Fish Shellfish Immunol.* 35: 2017-2019.

Korytář T, Wiegertjes G F, Zusková E, Tomanová A, Lisnerová M, Patra S, Sieranski V, Šima R, Born-Torrijos A, Wentzel A S, Blasco-Monleon S, Yanes-Roca C, Policar T, Holzer A S (2019) The kinetics of cellular and humoral immune responses of common carp to presporogonic development of the myxozoan *Sphaerospora molnari. Parasit Vectors.* 2019;12: 208.

Lanham S M, Godfrey D G (1970) Isolation of salivarian trypanosomes from man and other mammals using DEAE-cellulose. *Exp Parasitol.* 28: 521-534.

Mohamad A. et al., MDPI, Vaccines 2021, 9, 368.

Oerskov, I. (1977). Serology, chemistry, and genetics of O and K antigens of *Escherichia coli. Bacteriol. Rev.* 41: 667-710.

Reister M[1], Hoffmeier K[2], Krezdorn N[3], Rotter B[4], Liang C[5], Rund S[6], Dandekar T[7], Sonnenborn U[8], Oelschlaeger T A[9]. Complete genome sequence of the gram-negative probiotic *Escherichia coli* strain Nissle 1917. J Biotechnol. 2014 Oct. 10; 187:106-7. doi: 10.1016/j.jbiotec.2014.07.442. Epub 2014 Aug. 2.

Yilmaz, B.; Portugal, S.; Tran, T. M.; Gozzelino, R.; Ramos, S.; Gomes, J.; Regalado, A.; Cowan, P. J.; d'Apice, A. J.; Chong, A. S.; et al. Gut microbiota elicits a protective immune response against malaria transmission. *Cell.* 2014, 159, 1277-1289.

The invention claimed is:

1. A method for preventing and/or reducing, in a non-human animal that does not produce α-Gal, an infectious disease caused by a pathogen expressing α-Gal on its surface, comprising administering to the non-human animal an *E. coli* strain, wherein the *E. coli* strain is *E. coli* Nissle 1917 or *E. coli* O111, the infectious disease is sphaerosporis and the non-human animal is common carp or wherein the wherein the *E. coli* strain is *E. coli* O86:B7 or *E. coli* O111 the infectious disease is aspergillosis and the non-human animal is poultry.

2. The method according to claim 1, wherein the *E. coli* strain is *E. coli* Nissle 1917.

3. The method according to claim 1, wherein the *E. coli* strain is *E. coli* O111.

4. The method according to claim 1, wherein the non-human animal is a poultry.

5. The method according to claim 1, wherein the *E. coli* strain is *E. coli* O86:B7.

6. The method according to claim 1, wherein the *E. coli* strain is a feed additive.

7. The method according to claim 1, comprising administering from $1\times10^{7}$ CFU to $1\times10^{10}$ CFU (Colony-Forming Unit) of the *E. coli* strain.

8. The method according to claim 1, wherein the *E. coli* strain decreases proinflammatory anti α-Gal IgA to residual levels in the lungs of poultry or fish infected respectively with *aspergillus* or myxozoan pathogens expressing α-Gal.

9. The method according to claim 1, wherein the *E. coli* strain induces residual levels of anti α-Gal IgA and reduces lung lesions and inflammation.

10. The method according to claim 1, comprising oral administration of the *E. coli* strain at $1\times10^{7}$ CFU to $1\times10^{10}$ CFU (Colony-Forming Unit), per dose per animal.

11. A method for preventing and/or reducing, in a non-human animal that does not produce α-Gal, an infectious disease caused by a pathogen expressing α-Gal on its surface, comprising administering to the non-human animal an *E. coli* strain, wherein the *E. coli* is *E. coli* Nissle 1917, the non-human animal is fish, and the pathogen expressing α-Gal on its surface is a myxozoan parasite.

12. A method for preventing and/or reducing, in a non-human animal that does not produce α-Gal, an infectious disease caused by a pathogen expressing α-Gal on its surface, comprising administering to the non-human animal an *E. coli* strain, wherein the *E. coli* is *E. coli* O86:B7, the non-human animal is poultry, and the pathogen expressing α-Gal on its surface is an *Aspergillus*.

* * * * *